(12) United States Patent
Keane et al.

(10) Patent No.: US 11,759,355 B1
(45) Date of Patent: Sep. 19, 2023

(54) METHOD OF DELIVERING LEADING BLEBS AND AGENT TO SUBRETINAL SPACE

(71) Applicant: Gyroscope Therapeutics Limited, London (GB)

(72) Inventors: Michael F. Keane, Downingtown, PA (US); Thomas E. Meyer, Philadelphia, PA (US); Benjamin L. Ko, Cincinnati, OH (US)

(73) Assignee: Gyroscope Therapeutics Limited, London (GB)

( * ) Notice: Subject to any disclaimer, the term of this patent is extended or adjusted under 35 U.S.C. 154(b) by 567 days.

(21) Appl. No.: 16/797,072

(22) Filed: Feb. 21, 2020

Related U.S. Application Data

(60) Provisional application No. 62/810,398, filed on Feb. 26, 2019.

(51) Int. Cl.
*A61F 9/007* (2006.01)
*A61F 9/00* (2006.01)
(Continued)

(52) U.S. Cl.
CPC .......... *A61F 9/0017* (2013.01); *A61F 9/0008* (2013.01); *A61F 9/0026* (2013.01);
(Continued)

(58) Field of Classification Search
CPC .... A61F 9/0017; A61F 9/0026; A61F 9/0008; A61F 9/00; A61F 9/007; A61F 9/00736; A61F 2/14; A61F 2009/00863; A61F 9/00727; A61F 2009/00891; A61N 5/1017; A61K 9/0048; A61K 9/0051;
(Continued)

(56) References Cited

U.S. PATENT DOCUMENTS

| 4,573,979 | A | * | 3/1986 | Blake ..................... A61M 1/85 604/35 |
| 5,409,457 | A | | 4/1995 | del Cerro et al. |

(Continued)

OTHER PUBLICATIONS

Chalberg, Thomas W., et al. "Gene transfer to rabbit retina with electron avalanche transfection." *Investigative ophthalmology & visual science* 47.9 (2006): 4083-4090.
(Continued)

*Primary Examiner* — Kai H Weng
*Assistant Examiner* — Brandon W. Levy
(74) *Attorney, Agent, or Firm* — Frost Brown Todd LLP

(57) ABSTRACT

A method includes inserting a flexible cannula between a sclera and a choroid of an eye. The needle is advanced from a distal end of the flexible cannula, such that the needle pierces the choroid to access a subretinal space of the eye. The needle is used to deliver a first volume of leading bleb fluid to the subretinal space. The delivery of leading bleb fluid is ceased for a duration of time. After expiration of the duration of time, the needle is used to deliver a second volume of the leading bleb fluid to the subretinal space. The combination of the delivered first and second volumes of the leading bleb fluid causes a substantial portion of the retina to detach from the choroid. A therapeutic agent may then be delivered to the subretinal space in the region where the retina is detached from the choroid.

19 Claims, 20 Drawing Sheets

(51) Int. Cl.
    *A61M 5/24*     (2006.01)
    *A61B 17/34*     (2006.01)
    *A61M 5/20*     (2006.01)
    *A61M 5/158*     (2006.01)

(52) U.S. Cl.
    CPC ...... *A61F 9/00727* (2013.01); *A61F 9/00736* (2013.01); *A61M 5/158* (2013.01)

(58) Field of Classification Search
    CPC ............... A61P 27/02; A61M 5/158; A61M 2210/0612; A61M 5/20; A61M 25/065; A61L 2430/16; A61B 17/3421
    See application file for complete search history.

(56) References Cited

U.S. PATENT DOCUMENTS

| | | | |
|---|---|---|---|
| 6,761,724 | B1 | 7/2004 | Zrenner et al. |
| 7,413,734 | B2 | 8/2008 | Mistry et al. |
| 2005/0143363 | A1 | 6/2005 | De Juan et al. |
| 2008/0058704 | A1 | 3/2008 | Hee et al. |
| 2008/0154204 | A1 | 6/2008 | Varner et al. |
| 2008/0281292 | A1 | 11/2008 | Hickingbotham et al. |
| 2010/0081707 | A1* | 4/2010 | Ali ................... A61P 27/02 604/151 |
| 2010/0191176 | A1* | 7/2010 | Ho ..................... A61F 9/008 606/4 |
| 2010/0305514 | A1 | 12/2010 | Valenti et al. |
| 2012/0191064 | A1* | 7/2012 | Conston .......... A61F 9/00727 604/523 |
| 2014/0276329 | A1* | 9/2014 | Urbaniak ............ A61K 35/28 604/8 |
| 2015/0223977 | A1 | 8/2015 | Oberkircher et al. |
| 2015/0351958 | A1 | 12/2015 | Contiliano et al. |
| 2015/0351959 | A1 | 12/2015 | Clem et al. |
| 2016/0074211 | A1 | 3/2016 | Ko et al. |
| 2016/0074212 | A1 | 3/2016 | Price et al. |
| 2016/0074217 | A1 | 3/2016 | Price et al. |
| 2016/0081849 | A1 | 3/2016 | Tsai et al. |
| 2017/0258988 | A1 | 9/2017 | Meyer et al. |
| 2017/0360605 | A1 | 12/2017 | Oberkircher et al. |
| 2017/0360606 | A1 | 12/2017 | Price et al. |
| 2017/0360607 | A1* | 12/2017 | Price ................. A61F 9/0008 |
| 2018/0256394 | A1 | 9/2018 | Price et al. |

OTHER PUBLICATIONS

Einmahl, Suzanne, et al. "Evaluation of a novel biomaterial in the suprachoroidal space of the rabbit eye." *Investigative ophthalmology & visual science* 43.5 (2002): 1533-1539.

Geroski, Dayle H., and Henry F. Edelhauser. "Drug delivery for posterior segment eye disease." *Investigative ophthalmology & visual science* 41.5 (2000): 961-964.

Machemer, Robert, and Ulrich H. Steinhorst. "Retinal separation, retinotomy, and macular relocation I. Experimental studies in the rabbit eye." *Graefe's archive for clinical and experimental ophthalmology* 231.11 (1993): 629-634.

Sternberg, Paul, et al. "Controlled aspiration of subretinal fluid in the diagnosis of carcinoma metastatic to the choroid." *Archives of Ophthalmology* 102.11 (1984): 1622-1625.

Kang, Se Woong, et al. "A new instrument for drainage or injection of fluid within subretinal space." *Retina* 23.5 (2003): 661-666.

Komáromy, András M., et al. "Application of a new subretinal injection device in the dog." *Cell transplantation* 15.6 (2006): 511-519.

Olsen, Timothy W., et al. "Cannulation of the suprachoroidal space: a novel drug delivery methodlgy to the posterior segment." *American journal of ophthalmology* 142.5 (2006): 777-787.

Patel, S. R., et al. "Intraocular Pharmacokinetics of Suprachoroidal Drug Deliver Administered Using Hollow Microneedles." *Invesitigative Ophthalmology & Visual Science* 51.13 (2010): 3796-3796.

Patel, S., et al. "Suprachoroidal Drug Delivery Using Microneedles." *Investigative Ophthalmology & Visual Science* 49.13 (2008): 5006-5006.

Patel, Samirkumar R., et al. "Suprachoroidal drug delivery to the back of the eye using hollow microneedles." *Pharmaceutical research* 28.1 (2011): 166-176.

Peden, M. C., et al. "Safety Study of Ab-Externo AAV Gene Therapy Delivery to the Subretinal and Suprachoroidal Space Using a 250 Micron Fleixble Microcatheter." *Investigative Ophthalmology & Visual Science* 50.13 (2009): 1450-1450.

Schanze, Thomas, et al. "Implantation and testing of subretinal film electrodes in domestic pigs." *Experimental eye research* 82.2 (2006): 332-340.

Soni, M. H., and A. K. Tyagi. "Induction of Choroidal Detachment: A New Surgical Technique for Choroidal Biopsy." *Investigative Ophthalmology & Visual Science* 46.13 (2005): 5438-5438.

* cited by examiner

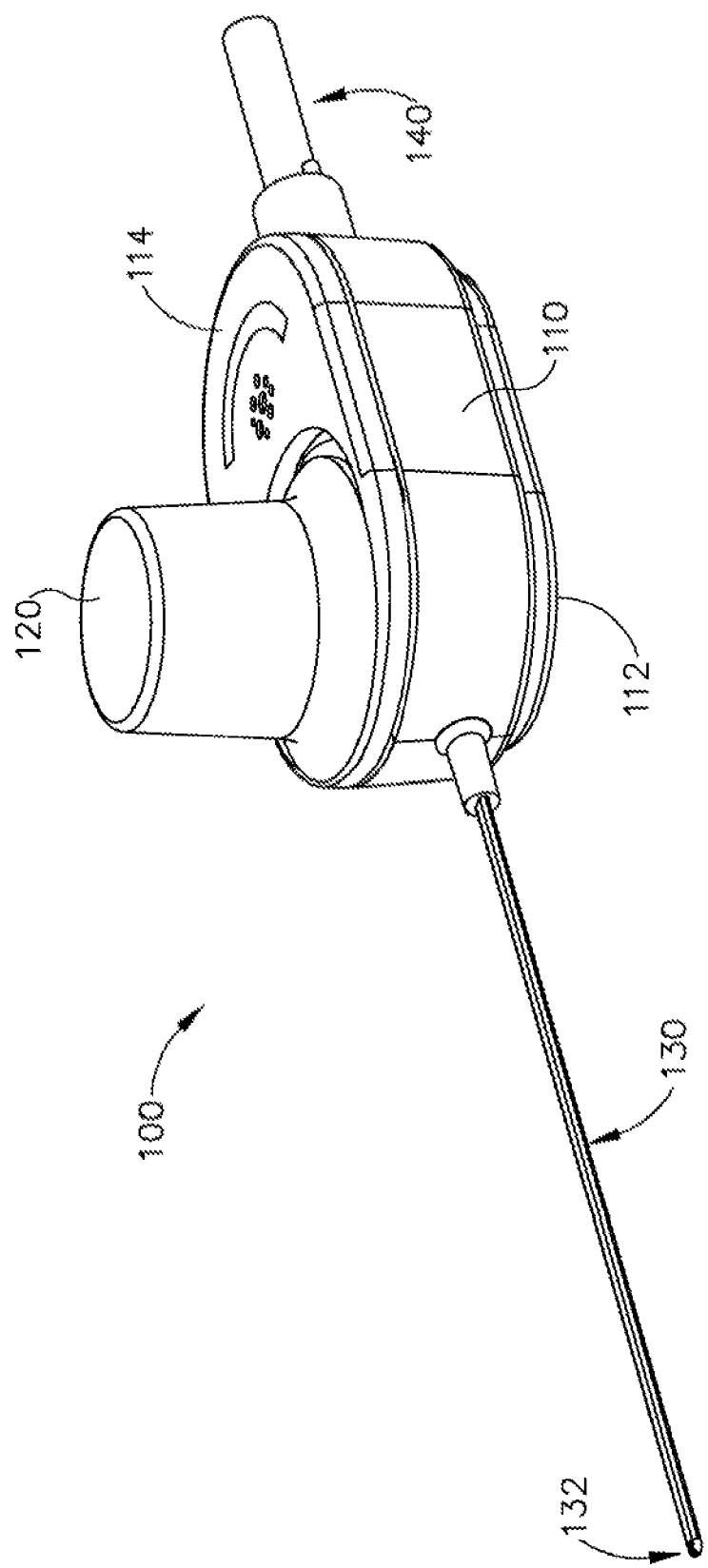

US 11,759,355 B1

METHOD OF DELIVERING LEADING BLEBS AND AGENT TO SUBRETINAL SPACE

PRIORITY

This application claims priority to U.S. Provisional Pat. App. No. 62/810,398, entitled "Method of Delivering Leading Blebs and Agent to Subretinal Space," filed Feb. 26, 2019, the disclosure of which is incorporated by reference herein in its entirety.

BACKGROUND

The human eye comprises several layers. The white outer layer is the sclera, which surrounds the choroid layer. The retina is interior to the choroid layer. The sclera contains collagen and elastic fiber, providing protection to the choroid and retina. The choroid layer includes vasculature providing oxygen and nourishment to the retina. The retina comprises light sensitive tissue, including rods and cones. The macula is located at the center of the retina at the back of the eye, generally centered on an axis passing through the centers of the lens and cornea of the eye (i.e., the optic axis). The macula provides central vision, particularly through cone cells.

Macular degeneration is a medical condition that affects the macula, such that people suffering from macular degeneration may experience lost or degraded central vision while retaining some degree of peripheral vision. Macular degeneration may be caused by various factors such as age (also known as "AMD") and genetics. Macular degeneration may occur in a "dry" (nonexudative) form, where cellular debris known as drusen accumulates between the retina and the choroid, resulting in an area of geographic atrophy. Macular degeneration may also occur in a "wet" (exudative) form, where blood vessels grow up from the choroid behind the retina. Even though people having macular degeneration may retain some degree of peripheral vision, the loss of central vision may have a significant negative impact on the quality of life. Moreover, the quality of the remaining peripheral vision may be degraded and, in some cases, may disappear as well. It may therefore be desirable to provide treatment for macular degeneration to prevent or reverse the loss of vision caused by macular degeneration. In some cases, it may be desirable to provide such treatment in a highly localized fashion, such as by delivering a therapeutic substance in the subretinal layer (under the neurosensory layer of the retina and above the retinal pigment epithelium) directly adjacent to the area of geographic atrophy, near the macula. However, since the macula is at the back of the eye and underneath the delicate layer of the retina, it may be difficult to access the macula in a practical fashion.

While a variety of surgical methods and instruments have been made and used to treat an eye, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 1 depicts a perspective view of an exemplary instrument for subretinal administration of a therapeutic agent from a suprachoroidal approach;

Figure 2A:
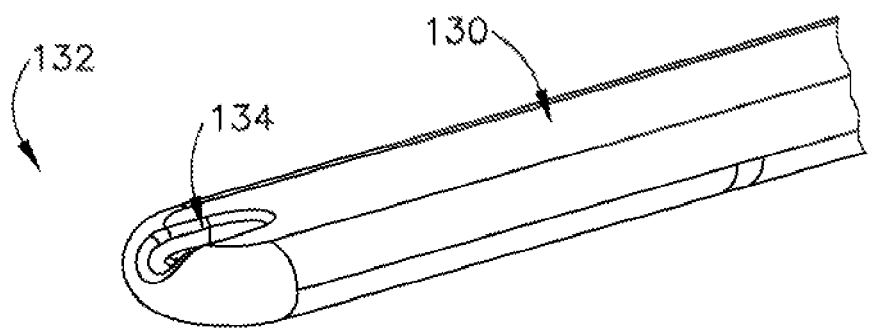
FIG. 2A depicts a perspective view of the distal end of a cannula of the instrument of FIG. 1, with a needle retracted in the cannula.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Instrument for Subretinal Administration of Therapeutic Agent

FIG. 1 shows an exemplary instrument (100) that is configured for use in a procedure for the subretinal administration of a therapeutic agent to an eye of a patient from a suprachoroidal approach. Instrument (100) comprises a body (110) and a flexible cannula (130) extending distally from body (110). Cannula (130) of the present example has a generally rectangular cross section, though any other suitable cross-sectional profile (e.g., elliptical, etc.) may be used. Cannula (130) is generally configured to support a needle (150) that is slidable within cannula (130), as will be described in greater detail below.

Figure 2B:
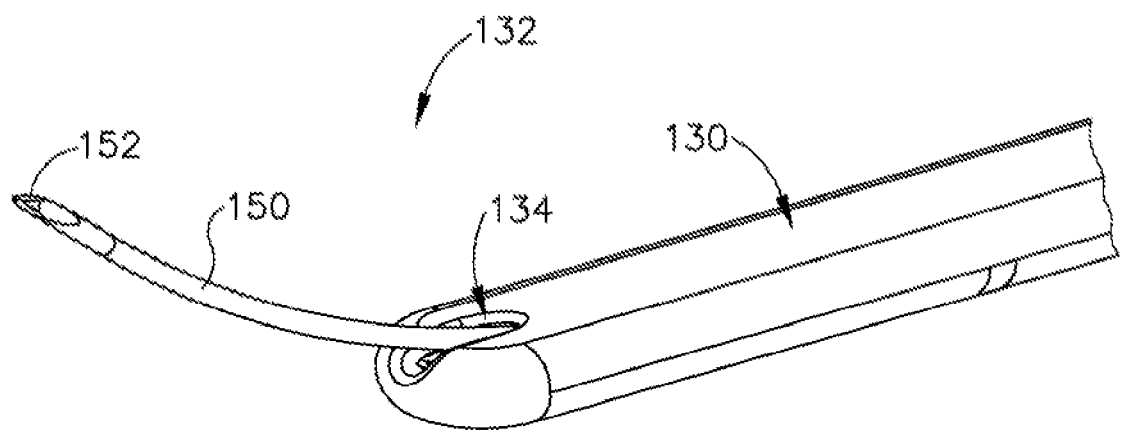
FIG. 2B depicts a perspective view of the distal end of a cannula of FIG. 2A, with a needle extending from the cannula.

In the present example, cannula (130) comprises a flexible material such as Polyether block amide (PEBA), which may be manufactured under the trade name PEBAX. Of course, any other suitable material or combination of materials may be used. Also in the present example, cannula (130) has a cross-sectional profile dimension of approximately 1.6 mm (width) by approximately 0.6 mm (height), with a length of approximately 80 mm. Alternatively, any other suitable dimensions may be used. Cannula (130) of the present example is flexible enough to conform to specific structures and contours of the patient's eye, yet cannula (130) has sufficient column strength to permit advancement of cannula (130) between the sclera and choroid of patient's eye without buckling. As best seen in FIGS. 2A-2B, cannula (130) includes a transversely oriented opening (134) at the distal end (132) of cannula (130). Distal end (132) is atraumatic such that distal end (132) is configured to provide separation between the sclera and choroid layers, as will be described in greater detail below, to thereby enable cannula (130) to be advanced between such layers while not inflicting trauma to the sclera or choroid layers.

By way of example only, cannula (130) may be configured and operable in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein; U.S. Pub. No. 2017/0360607, entitled "Apparatus and Method to From Entry Bleb for Subretinal Delivery of Therapeutic Agent," published Dec. 21, 2017, the disclosure of which is incorporated by reference herein; and/or U.S. Pub. No. 2017/0360606, entitled "Injection Device for Subretinal Delivery of Therapeutic Agent," published Dec. 21, 2017, the disclosure of which is incorporated by reference herein.

As shown in FIG. 2B, needle (150) may be advanced distally to protrude from opening (134). Needle (150) of the present example has a sharp distal tip (152) and defines a lumen (not shown). Distal tip (152) of the present example has a lancet configuration. In some other versions, distal tip (152) has a tri-bevel configuration or any other configuration as described in U.S. Pub. No. 2015/0223977, entitled "Method and Apparatus for Subretinal Administration of Therapeutic Agent," published Aug. 13, 2015, the disclosure of which is incorporated by reference herein. Still other suitable forms that distal tip (152) may take will be apparent to those of ordinary skill in the art in view of the teachings herein.

Needle (150) of the present example comprises a stainless steel hypodermic needle that is sized to deliver and aspirate fluids while being small enough to minimize incidental trauma as needle (150) penetrates tissue structures of the patient's eye, as will be described in greater detail below. While stainless steel is used in the present example, any other suitable material(s) may be used, including but not limited to nitinol, etc.

By way of example only, needle (150) may be 35 gauge with a 100 μm inner diameter, although other suitable sizes may be used. For instance, the outer diameter of needle (150) may fall within the range of 27 gauge to 45 gauge; or more particularly within the range of 30 gauge to 42 gauge; or more particularly within the range of 32 gauge to 39 gauge. As another merely illustrative example, the inner diameter of needle (150) may fall within the range of approximately 50 µm to approximately 200 µm; or more particularly within the range of approximately 50 µm to approximately 150 µm; or more particularly within the range of approximately 75 µm to approximately 125 µm.

In some versions, a needle guide (not shown) is disposed within cannula (130) to guide needle (150) along a predefined angle as needle (150) exits through opening (134). By way of example only, the exit angle for needle (150) may be within the range of approximately 5° to approximately 30° relative to the longitudinal axis of cannula (130); or more particularly within the range of approximately 5° to approximately 20° relative to the longitudinal axis of cannula (130); or more particularly within the range of approximately 5° to approximately 10° relative to the longitudinal axis of cannula (130); or more particularly within the range of approximately 7° and approximately 9° relative to the longitudinal axis of cannula (130). In addition to or in lieu of providing a needle guide within cannula (130), needle (150) may be resiliently biased to assume a bent configuration to thereby provide an exit angle that varies based on the extent to which needle (130) is advanced distally relative to cannula (130). By way of example only, needle (150) may include a preformed bend in accordance with at least some of the teachings of U.S. Pub. No. 2017/0258988, entitled "Apparatus for Subretinal Administration of Therapeutic Agent via a Curved Needle," published Sep. 14, 2017, the disclosure of which is incorporated by reference herein.

As shown in FIG. 1, instrument (100) of the present example further comprises an actuation knob (120) located at a top portion (114) of body (110). Actuation knob (120) is rotatable relative to body (110) to thereby selectively translate needle (150) longitudinally relative to cannula (130). In particular, actuation knob (120) is rotatable in a first angular direction to drive needle (150) distally relative to cannula (130); and in a second angular direction to drive needle (150) proximally relative to cannula (130). By way of example only, instrument (100) may provide such functionality through knob (120) in accordance with at least some of the teachings of U.S. Pub. No. 2017/0360606, the disclosure of which is incorporated by reference herein; and/or U.S. Pub. No. 2017/0360607, the disclosure of which is incorporated by reference herein. Other suitable ways in which rotary motion of knob (120) may be converted to linear translation of needle (150) will be apparent to those of ordinary skill in the art in view of the teachings herein. Similarly, other suitable ways in which needle (150) may be actuated (150) longitudinally relative to cannula (130) will be apparent to those of ordinary skill in the art in view of the teachings herein.

As also shown in FIG. 1, a conduit assembly (140) extends proximally from body (110). Conduit assembly (140) is configured to contain one or more fluid conduits (not shown) that are in fluid communication with needle (150). Such fluid conduits may comprise one or more flexible tubes, etc. In some versions, conduit assembly (140) also contains one or more wires. By way of example only, such wires may provide communication of data signals from one or more sensors in body (110) to a processor that is remote from instrument (100). Such a configuration and operability may be carried out in accordance with at least some of the teachings of U.S. Pub. No. 2017/0360606, the disclosure of which is incorporated by reference herein; and/or U.S. Pub. No. 2017/0360607, the disclosure of which is incorporated by reference herein. By way of further example only, such wires may provide communication of electrical power to one or more electrically powered components in body (110). Various suitable ways in which electrical power and/or signals may be implemented through one or more wires in conduit assembly (140) and one or more electrically associated components in body (110) will be apparent to those of ordinary skill in the art in view of the teachings herein. Alternatively, some versions of conduit assembly (140) may lack wires altogether; and body (110) may lack sensors, electrically powered components, etc.

The features and operability of instrument (100) may be varied in numerous ways. In addition, instrument (100) may be modified in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein; U.S. Pub. No. 2015/0351958, entitled "Therapeutic Agent Delivery Device with Convergent Lumen," published Dec. 10, 2015, the disclosure of which is incorporated by reference herein; U.S. Pub. No. 2015/0351959, entitled "Sub-Retinal Tangential Needle Catheter Guide and Introducer," published Dec. 10, 2015, the disclosure of which is incorporated by reference herein; U.S. Pub. No. 2016/0074212, entitled "Method and Apparatus for Sensing Position Between Layers of an Eye," published Mar. 17, 2016, the disclosure of which is incorporated by reference herein; U.S. Pub. No. 2016/0074217, entitled "Motorized Suprachoroidal Injection of Therapeutic Agent," published Mar. 17, 2016, the disclosure of which is incorporated by reference herein; U.S. Pub. No. 2016/0074211, entitled "Therapeutic Agent Delivery Device with Advanceable Cannula and Needle," published Mar. 17, 2016, the disclosure of which is incorporated by reference herein; and/or U.S. Pub. No. 2016/0081849, entitled "Therapeutic Agent Delivery Device," published Mar. 24, 2016, the disclosure of which is incorporated by reference herein. Other suitable modifications will be apparent to those of ordinary skill in the art in view of the teachings herein.

II. Exemplary Procedure for Inducing Retinal Detachment to Enhance Delivery of a Therapeutic Agent As described in U.S. Pub. No. 2015/0223977, the disclosure of which is incorporated by reference herein; U.S. Pub. No. 2017/0360606, the disclosure of which is incorporated by reference herein; and U.S. Pub. No. 2017/0360607, the disclosure of which is incorporated by reference herein, it may be desirable to inject a therapeutic agent into the subretinal space of an eye (20) to treat macular degeneration or some other condition. By way of example only, the therapeutic agent may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. It should nevertheless be understood that instrument (100) and the exemplary methods described herein are not intended to necessarily be limited to treatment of the particular medical conditions that are specifically identified herein. A non-exhaustive, non-limiting listing of other conditions that may be addressed by instrument (100) and the exemplary methods described herein may include diabetic macular edema, inherited retinal diseases, retinitis pigmentosa, retinal vein occlusion, diabetic retinopathy, posterior uveitis, Stargardt disease, etc.

In the procedures described in U.S. Pub. No. 2015/0223977, U.S. Pub. No. 2017/0360606, and U.S. Pub. No. 2017/0360607, a relatively small volume of a leading bleb fluid (e.g., balanced salt solution or "BSS") is injected into the subretinal space to provide a barrier between distal tip (152) of needle (150) and the retina (26), to thereby reduce the risk of the retina (26) being inadvertently pierced by distal tip (152). In these procedures, the relatively small volume (e.g., approximately 50 μL) of leading bleb fluid provides a highly localized separation of the retina (26) from the choroid (24). A relatively small volume (e.g., approximately 50 μL) of therapeutic agent is then delivered to this same region of subretinal space, mixing with the leading bleb fluid. As the therapeutic agent is delivered to the subretinal space, the additional volume may provide some degree of additional separation of the retina (26) from the choroid (24), though this separation may still be substantially localized and only apply to a relatively small region of the retina (26). The therapeutic agent is primarily absorbed by the relatively small region of the retina (26) that was separated from the choroid (24) by the leading bleb fluid and the therapeutic agent.

In some scenarios, it may be desirable to enhance the absorption of the therapeutic agent by increasing the surface area of the retina (26) that is directly exposed to the therapeutic agent. This may be carried out by providing additional, intentional separation of the retina (26) from the choroid (24). As described in U.S. Pub. No. 2018/0256394, entitled "Method of Performing Subretinal Drainage and Agent Delivery," published Sep. 13, 2018, the disclosure of which is incorporated by reference herein, a substantial region of the retina (26) may be intentionally separated from the choroid (24) by injecting a substantial volume of leading bleb fluid to the subretinal space. Another merely illustrative example of such a procedure is described in greater detail below.

Figure 3:
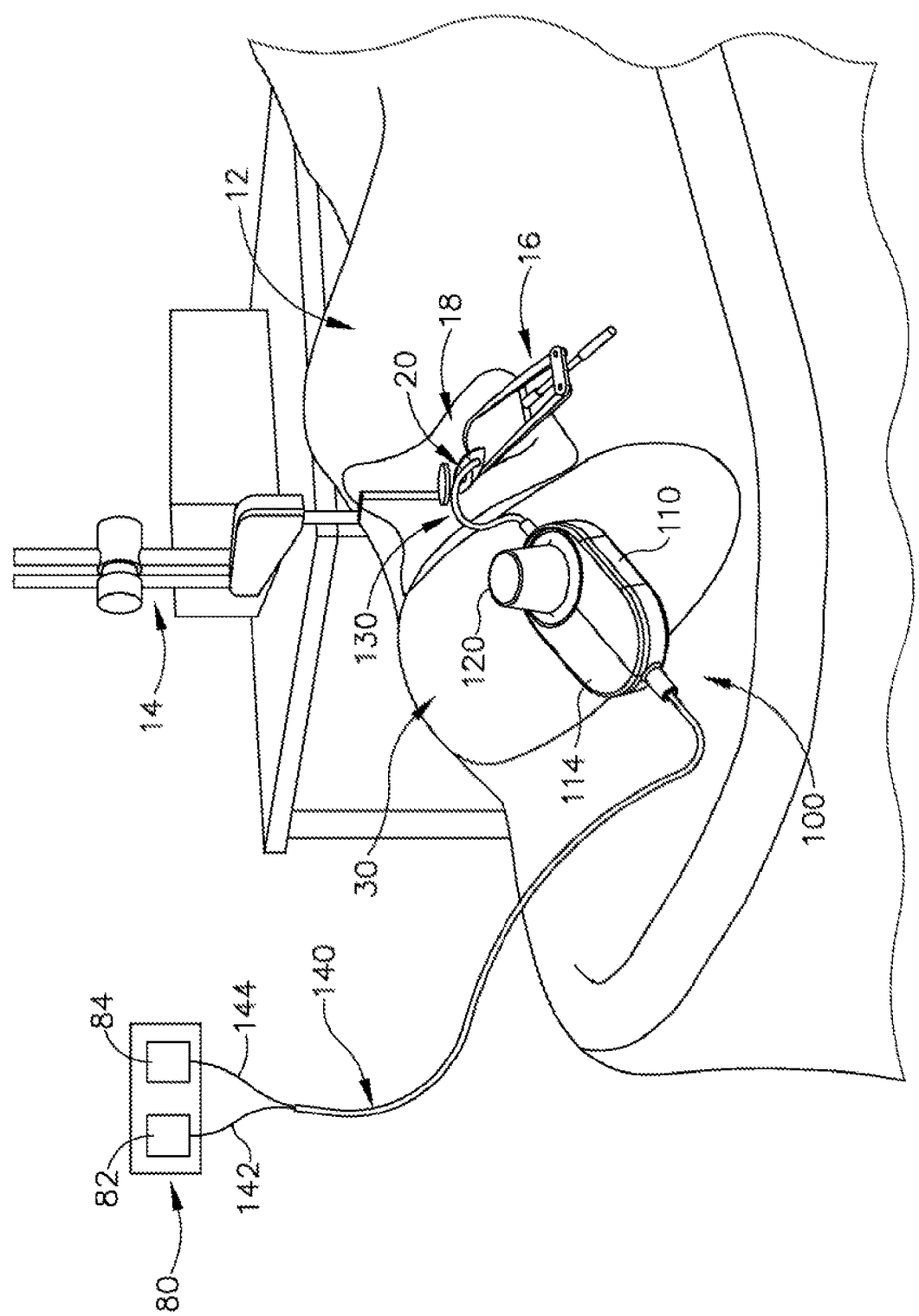
FIG. 3 depicts a perspective view of the instrument of FIG. 1, mounted near a patient, in combination with a first exemplary combination of medical equipment.

In the scenario of FIG. 3, instrument (100) is positioned in relation to a patient. In this example, a drape (12) is disposed over the patient, with an opening (18) formed in drape (12) near the patient's eye (20). A speculum (16) is used to keep the eye (20) open. A fixture (14) is positioned adjacent to the eye (20). Fixture (14) may be used to secure instrumentation, such as a viewing scope, relative to the patient. A magnetic pad (30) is adhered to drape (12) near the opening (18) adjacent to the eye (20). Instrument (100) is placed on magnetic pad (30); and is removably secured thereto via magnetic attraction. As noted above, one or more permanent magnets (not shown) are positioned within body (110) near bottom portion (112); and these magnets are magnetically attracted to one or more ferrous elements (not shown) contained within magnetic pad (30). As also noted above, these magnets and magnetic pad (30) may be configured in accordance with at least some of the teachings of U.S. Pub. No. 2017/0360606, the disclosure of which is incorporated by reference herein. Instrument (100) is oriented to enable insertion of flexible cannula (130) of instrument (100) into the eye (20). Exemplary processes for inserting and positioning cannula (130) in the eye (20) are described in greater detail below with reference to FIGS. 4A-4H and FIG. 5A-6B.

In the scenario shown in FIG. 3, instrument (100) is coupled with a fluid delivery system (80) via conduit assembly (140). In this example, fluid delivery system (80) comprises a bleb fluid source (82) and a therapeutic agent fluid source (84). Bleb fluid source (82) is coupled with a bleb fluid conduit (142) of conduit assembly (140); and therapeutic agent fluid source (84) is coupled with a therapeutic agent conduit (144) of conduit assembly (140). Conduits (142, 144) are in fluid communication with needle (150). In some versions, fluid sources (82, 84) comprise syringes. In some other versions, fluid sources (82, 84) comprise separate reservoirs and one or more associated pumps and/or valves, etc. By way of example only, fluid delivery system (80) may be configured and operable in accordance with at least some of the teachings of U.S. Pub. No. 2017/0360606, the disclosure of which is incorporated by reference herein; and/or U.S. Pub. No. 2017/0360607, the disclosure of which is incorporated by reference herein. Similarly, conduits (142, 144) may be in fluid communication with needle (150) in accordance with at least some of the teachings of U.S. Pub. No. 2017/0360606, the disclosure of which is incorporated by reference herein; and/or U.S. Pub. No. 2017/0360607, the disclosure of which is incorporated by reference herein. Other suitable configurations will be apparent to those of ordinary skill in the art in view of the teachings herein.

Figure 4A:
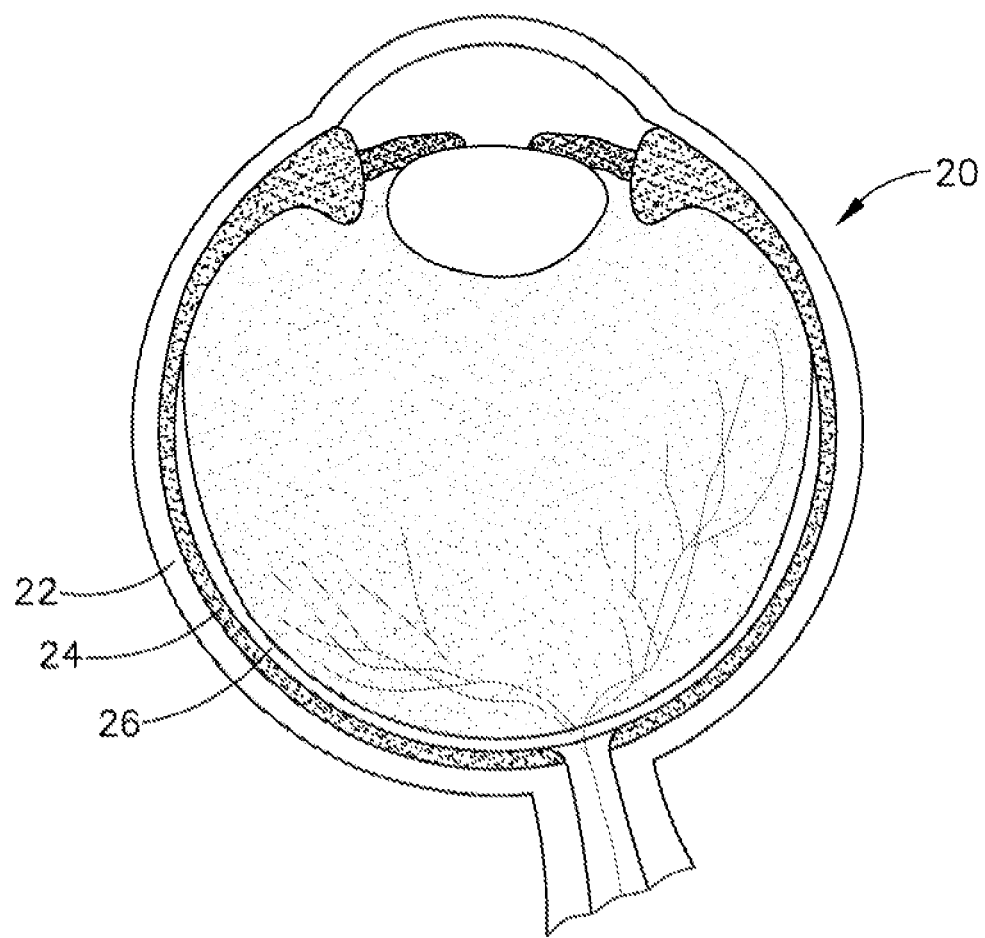
FIG. 4A depicts a cross-sectional side view of an eye of a patient.

A. Exemplary Subretinal Delivery of Substantial Volume of Leading Bleb Fluid from Single Suprachoroidal Site FIGS. 4A-4H show a procedure where instrument (100) is used to deliver a leading bleb fluid and a therapeutic agent to the subretial space of a patient's eye (20) from a single suprachoroidal site. FIG. 4A shows an eye (20) before the procedure is initiated. At this stage, the operator may immobilize tissue surrounding the patient's eye (20) (e.g., the eyelids), using speculum (16) and/or any other instrument suitable for immobilization. While immobilization described herein with reference to tissue surrounding eye (20), eye (20) itself may remain free to move. In some versions, once the tissue surrounding eye (20) has been immobilized, an eye chandelier port (not shown) is inserted into eye (20), to provide intraocular illumination when the interior of eye (20) is viewed through the pupil. Alternatively, an eye chandelier port need not necessarily be used.

Figure 4B:
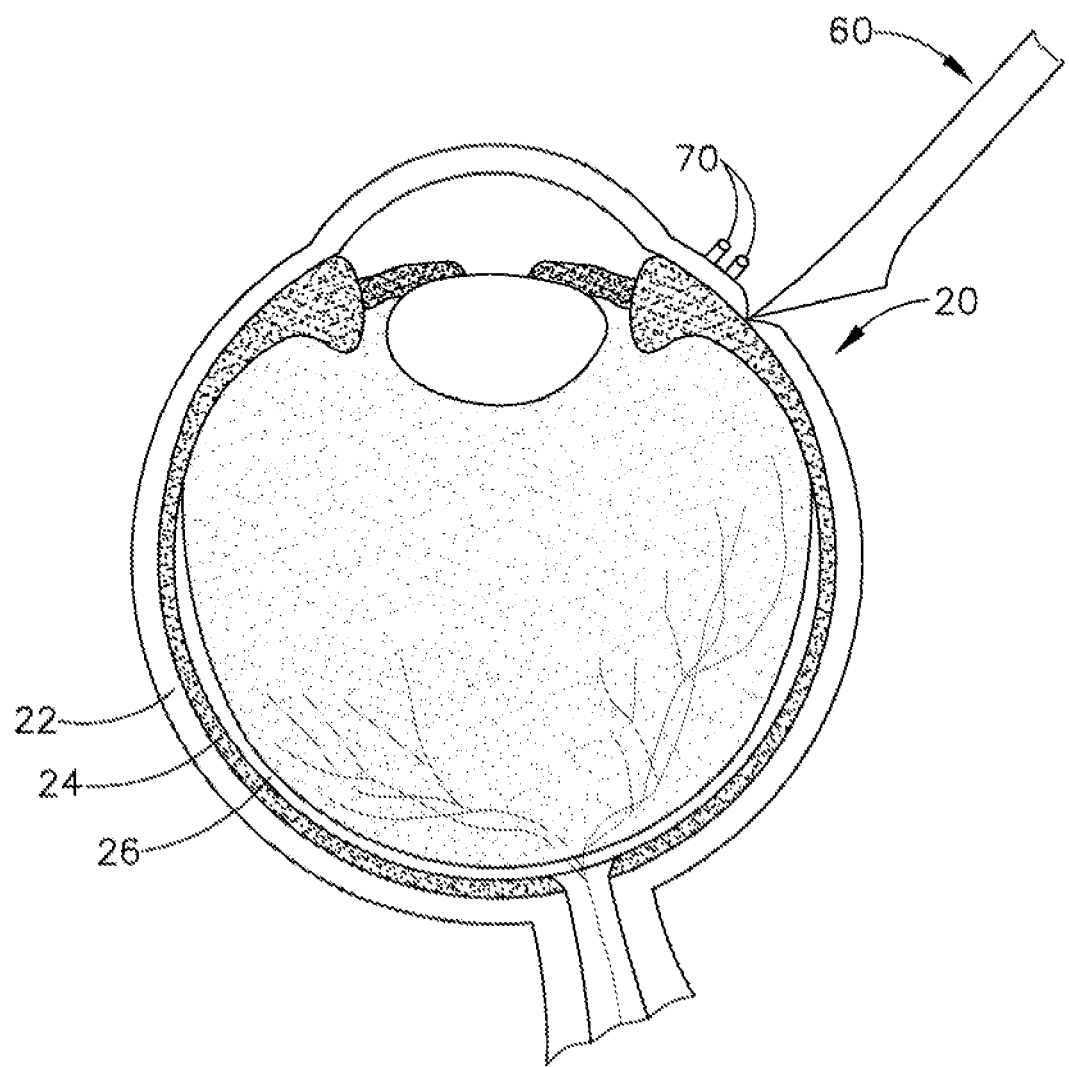
FIG. 4B depicts a cross-sectional side view of the eye of FIG. 4A, with a suture loop attached to the eye, and with a sclerotomy being performed.

Once the tissue surrounding the eye (20) has been sufficiently immobilized (and, optionally, an eye chandelier port installed), the sclera (22) may be accessed by dissecting the conjunctiva by incising a flap in the conjunctiva and pulling the flap posteriorly. After such a dissection is completed, the exposed surface of the sclera (22) may optionally be blanched using a cautery tool to minimize bleeding. Once conjunctiva dissection is complete, the exposed surface of the sclera (22) may optionally be dried using a WECK-CEL or other suitable absorbent device. A template may then be used to mark the eye (20), as described in U.S. Pub. No. 2015/0223977, the disclosure of which is incorporated by reference herein; and/or U.S. Pub. No. 2017/0360605, the disclosure of which is incorporated by reference herein. The operator may then use a visual guide created using the template to attach a suture loop assembly (70) and to perform a sclerotomy, as shown in FIG. 4B, using a conventional scalpel (60) or other suitable cutting instrument. By way of example only, suture loop assembly (70) may be formed in accordance with at least some of the teachings of U.S. Pub. No. 2015/0223977, the disclosure of which is incorporated by reference herein. Alternatively, in lieu of suture loop assembly (70), the operator may install a guide tack in accordance with at least some of the teachings of U.S. Pub. No. 2017/0360605, the disclosure of which is incorporated by reference herein.

The sclerotomy procedure with scalpel (60) forms a small incision through the sclera (22) of the eye (20). The sclerotomy is performed with particular care to avoid penetration of the choroid (24). Thus, the sclerotomy procedure provides access to the space between the sclera (22) and the choroid (24). Once the incision is made in the eye (20), a blunt dissection may optionally be performed to locally separate the sclera (22) from the choroid (24). Such a dissection may be performed using a small blunt elongate instrument, as will be apparent to those of ordinary skill in the art in view of the teachings herein.

Figure 4C:
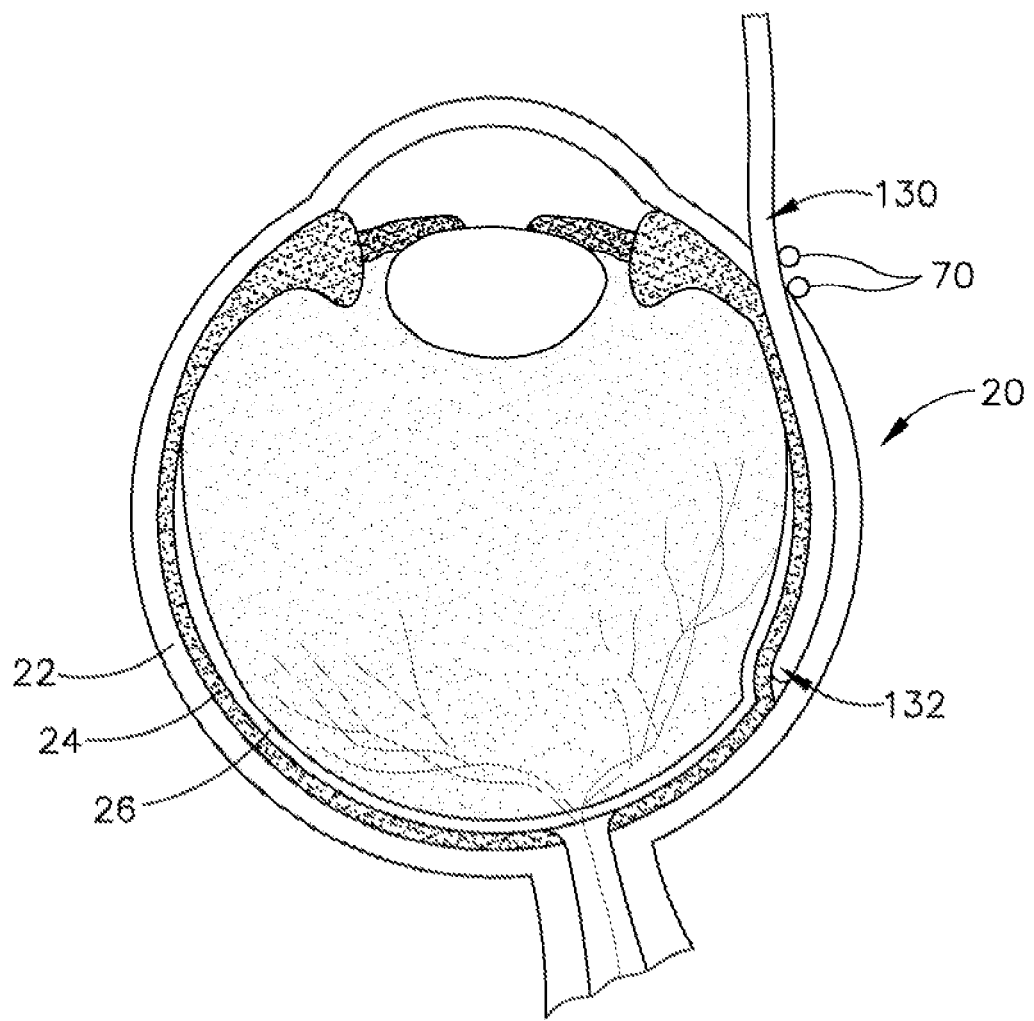
FIG. 4C depicts a cross-sectional side view of the eye of FIG. 4A, with the cannula of FIG. 2A being inserted through the sclerotomy opening and in between the sclera and choroid of the eye.

With the sclerotomy procedure performed, the operator may insert cannula (130) of instrument (100) through the incision and into the space between the sclera (22) and the choroid (24). As can be seen in FIG. 4C, cannula (130) is directed through suture loop assembly (70) and into the incision. Suture loop assembly (70) may stabilize cannula (130) during insertion. Additionally, suture loop assembly (70) maintains cannula (130) in a generally tangential orientation relative to the incision. Such tangential orientation may reduce trauma as cannula (130) is guided through the incision. As cannula (130) is inserted into the incision through suture loop assembly (70), an operator may use forceps or other instruments to further guide cannula (130) along an atraumatic path. Of course, use of forceps or other instrumentation is merely optional, and may be omitted in some examples. As noted above, a guide tack (or other device) may be used in lieu of suture loop assembly (70). Cannula (130) is advanced until distal end (132) is positioned at the posterior region of the retina (26). Various suitable ways of visualizing distal end (132) to thereby observe proper positioning of distal end (132) will be apparent to those of ordinary skill in the art in view of the teachings herein.

Figure 4D:
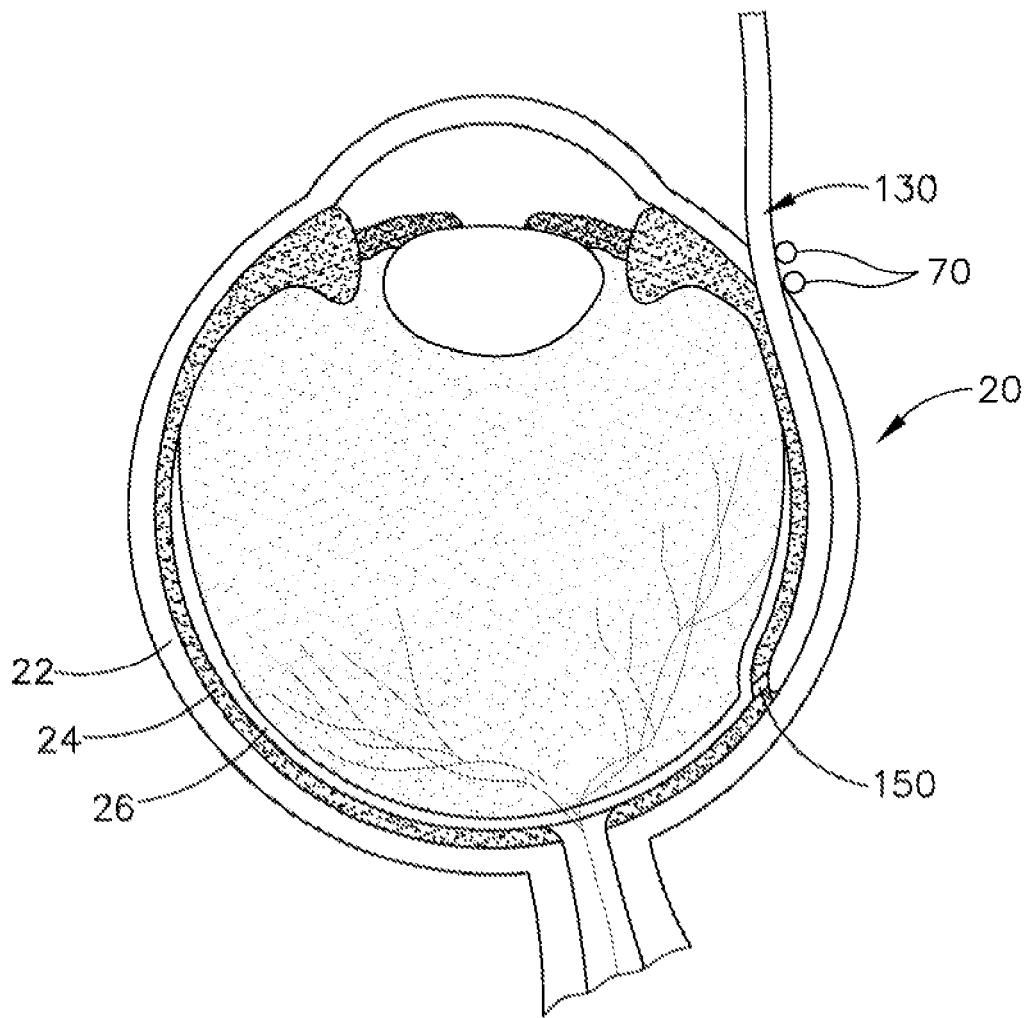
FIG. 4D depicts a cross-sectional side view of the eye of FIG. 4A, with the needle of FIG. 2B being advanced through the choroid to access the subretinal space.
Figure 4E:
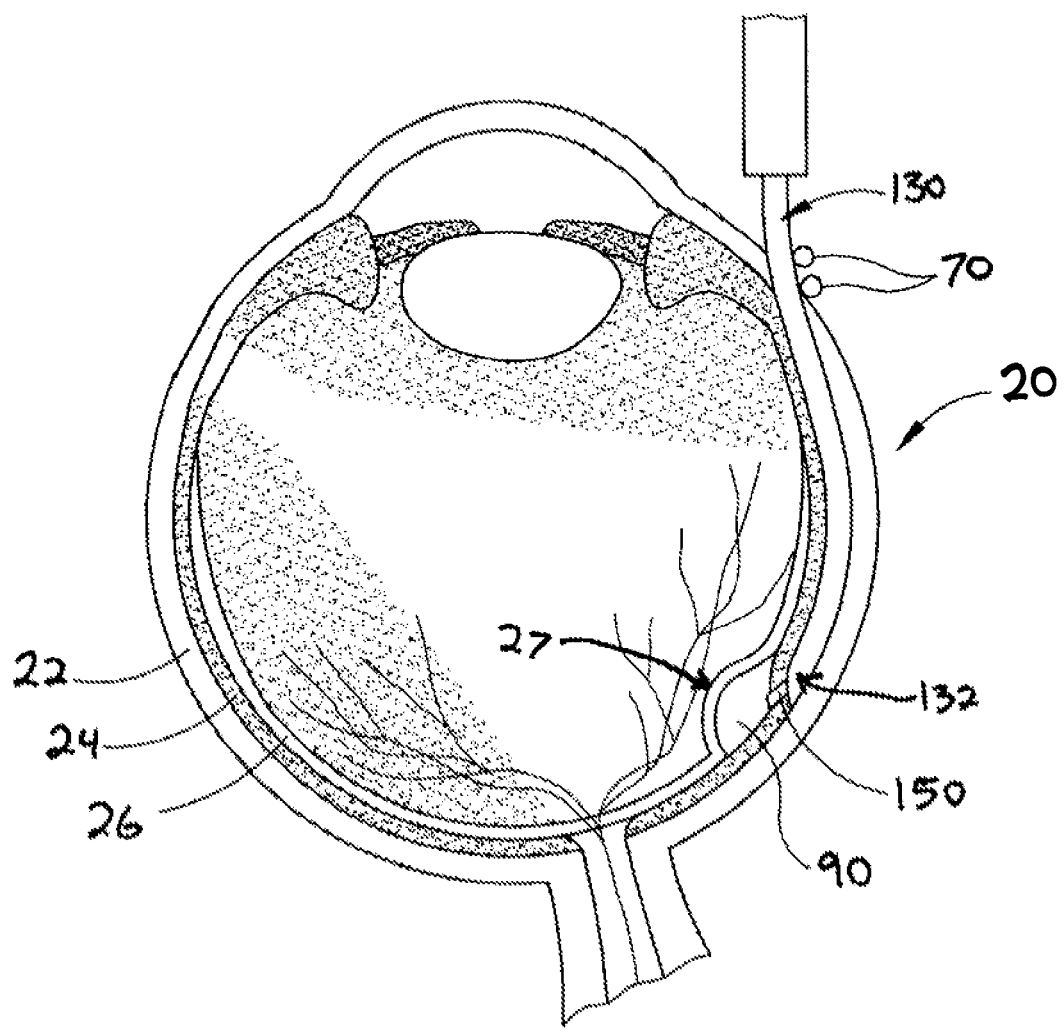
FIG. 4E depicts a cross-sectional side view of the eye of FIG. 4A, with the needle of FIG. 2B dispensing a first volume of leading bleb fluid to provide separation between a first region of the retina and the choroid.
Figure 4F:
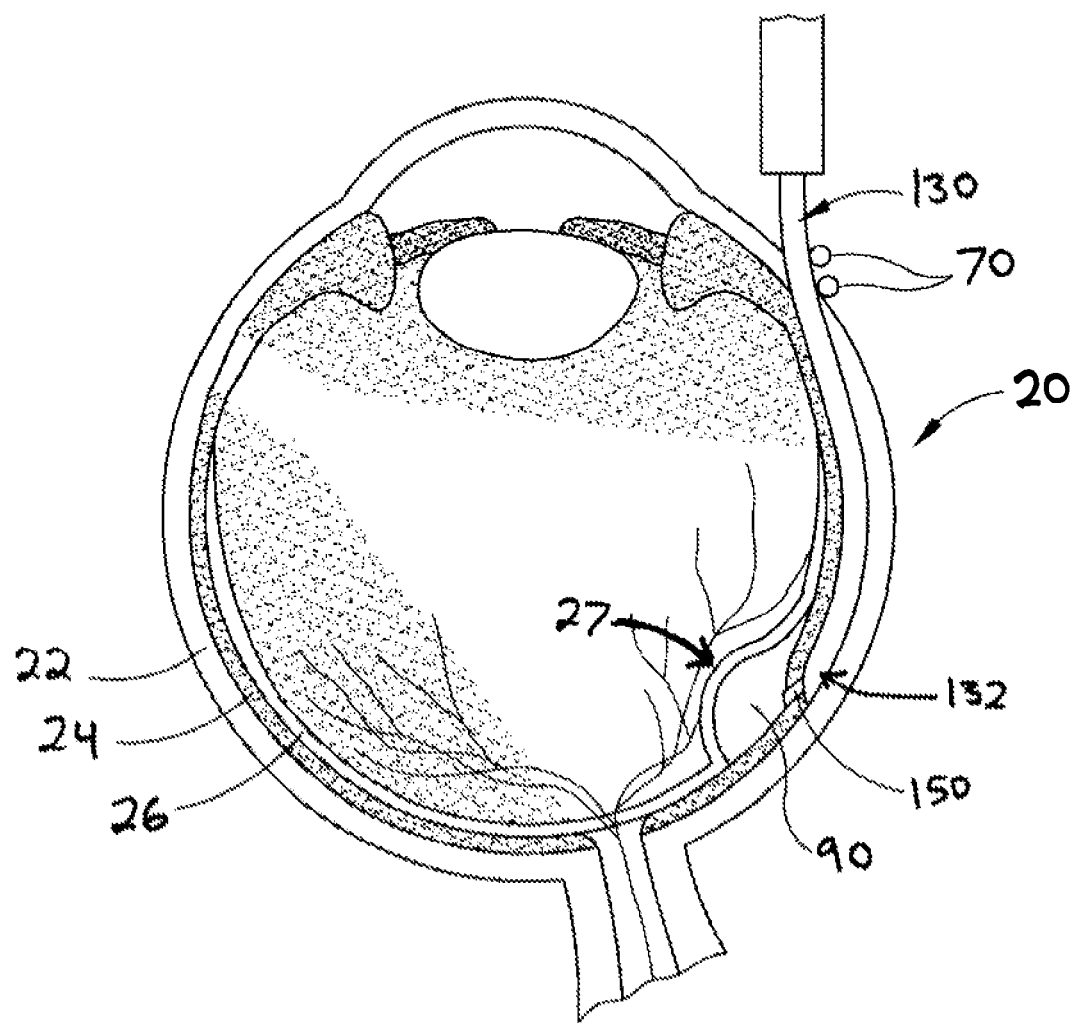
FIG. 4F depicts a cross-sectional side view of the eye of FIG. 4A, with the needle of FIG. 2B dispensing a second volume of leading bleb fluid to provide further separation between a second region of the retina and the choroid, the second region being larger than the first region.

Once cannula (130) has been advanced to the position shown in FIG. 4C, the operator may advance needle (150) of instrument (100) distally as described above by actuating knob (120). As can be seen in FIG. 4D, needle (150) is advanced relative to cannula (130) such that needle (150) pierces through the choroid (24) without penetrating the retina (26). The operator then actuates fluid delivery system (80) to drive bleb fluid from bleb fluid source (82), thereby delivering a first volume of bleb fluid (90) to the subretinal space, as shown in FIG. 4E. The operator may cease delivery of bleb fluid (90) for a predetermined period, then deliver a second volume of bleb fluid (90), as shown in FIG. 4F. The volume of delivered bleb fluid (90) formed by the combination of the first and second volumes (of FIGS. 4E and 4F, respectively) may be substantial. By way of example only, this combined volume of delivered bleb fluid (90) may be in the range of approximately 50 μL and approximately 700 μL, or more particularly in the range of approximately 150 μL and approximately 300 μL, or more particularly approximately 200 μL.

In the present example, the entire substantial volume of bleb fluid (90) is delivered in separate actuations of fluid delivery system (80). By way of example only, when the entire substantial volume of bleb fluid (90) is 200 μL, fluid delivery system (80) may be actuated one time to deliver 100 μL of bleb fluid (90); followed by a second actuation of fluid delivery system (80) to deliver a second 100 μL volume of bleb fluid (90). As yet another merely illustrative example, when the entire substantial volume of bleb fluid (90) is 150 μL, fluid delivery system (80) may be actuated one time to deliver 50 μL of bleb fluid (90); followed by a second actuation of fluid delivery system (80) to deliver a second 50 μL volume of bleb fluid (90); followed by a third actuation of fluid delivery system (80) to deliver a third 50 μL volume of bleb fluid (90).

In versions where the bleb fluid (90) is delivered via two or more separate actuations of fluid delivery system (80), the volumes delivered at each actuation may differ from each other. For instance, and by way of example only, when the entire substantial volume of bleb fluid (90) is 200 μL, fluid delivery system (80) may be actuated one time to deliver 50 μL of bleb fluid (90); followed by a second actuation of fluid delivery system (80) to deliver a 100 μL volume of bleb fluid (90); followed by a third actuation of fluid delivery system (80) to deliver another 50 μL of bleb fluid (90). The foregoing permutations are merely illustrative examples and are not intended to be limiting in any way. Other permutations of ways in which bleb fluid (90) may be delivered via two or more separate actuations of fluid delivery system (80) will be apparent to those skilled in the art in view of the teachings herein.

It should also be understood that, when the bleb fluid (90) is delivered via two or more separate actuations of fluid delivery system (80), the duration between the two or more separate actuations of fluid delivery system (80) may vary. By way of example only, the system or operator may wait for a duration from approximately 10 seconds to approximately 10 minutes between each actuation of fluid delivery system (80). In scenarios where the bleb fluid (90) is delivered via three or more separate actuations of fluid delivery system (80), the duration between the first and second actuations of fluid delivery system (80) may vary from the duration between the second and third actuations of fluid delivery system (80). In some such scenarios, the duration between the first and second actuations of fluid delivery system (80) may be longer than the duration between the second and third actuations of fluid delivery system (80). In other variations, the duration between the first and second actuations of fluid delivery system (80) may be shorter than the duration between the second and third actuations of fluid delivery system (80). Other ways in which the durations between fluid delivery system (80) actuations may vary will be apparent to those skilled in the art in view of the teachings herein.

In some versions where the bleb fluid (90) is delivered via two or more separate actuations of fluid delivery system (80), such as the exemplary procedure shown in FIGS. 4A-4H, needle (150) remains stationary throughout the separate actuations of fluid delivery system (80), such that the entirety of the bleb fluid (90) is delivered to the same region of the subretinal space. In some other versions, as will be described in greater detail below with reference to FIGS. 5A-6B, after a first volume of bleb fluid (90) is delivered to a first region of the subretinal space, needle (150) is retracted back into cannula (130) and cannula (130) is repositioned to another region of the suprachoroidal space. Needle (150) is then advanced again from cannula (130) into a second region of subretinal space; and a second volume of bleb fluid (90) is delivered to the second region of the subretinal space. In some versions of this procedure, the two regions of the subretinal space are positioned such that the first and second volumes of delivered bleb fluid (90) are adjacent to each other, combining to effectively form a single, relatively large volume of bleb fluid (90) in the subretinal space.

As shown in FIG. 4F, the substantial volume of bleb fluid (90) causes substantial separation of the retina (26) from the choroid (24), resulting in a substantially large detached portion (27) of the retina (26) along the posterior region of the eye (20). In other words, the substantial volume of bleb fluid (90) provides a substantial fluid dissection or hydraulic dissection between the retina (26) and the choroid (24). By way of example only, detached portion (27) be in the range of approximately 12 mm$^2$ to approximately 450 mm$^2$, or more particularly in the range of approximately 85 mm$^2$ to approximately 450 mm$^2$.

Figure 4G:
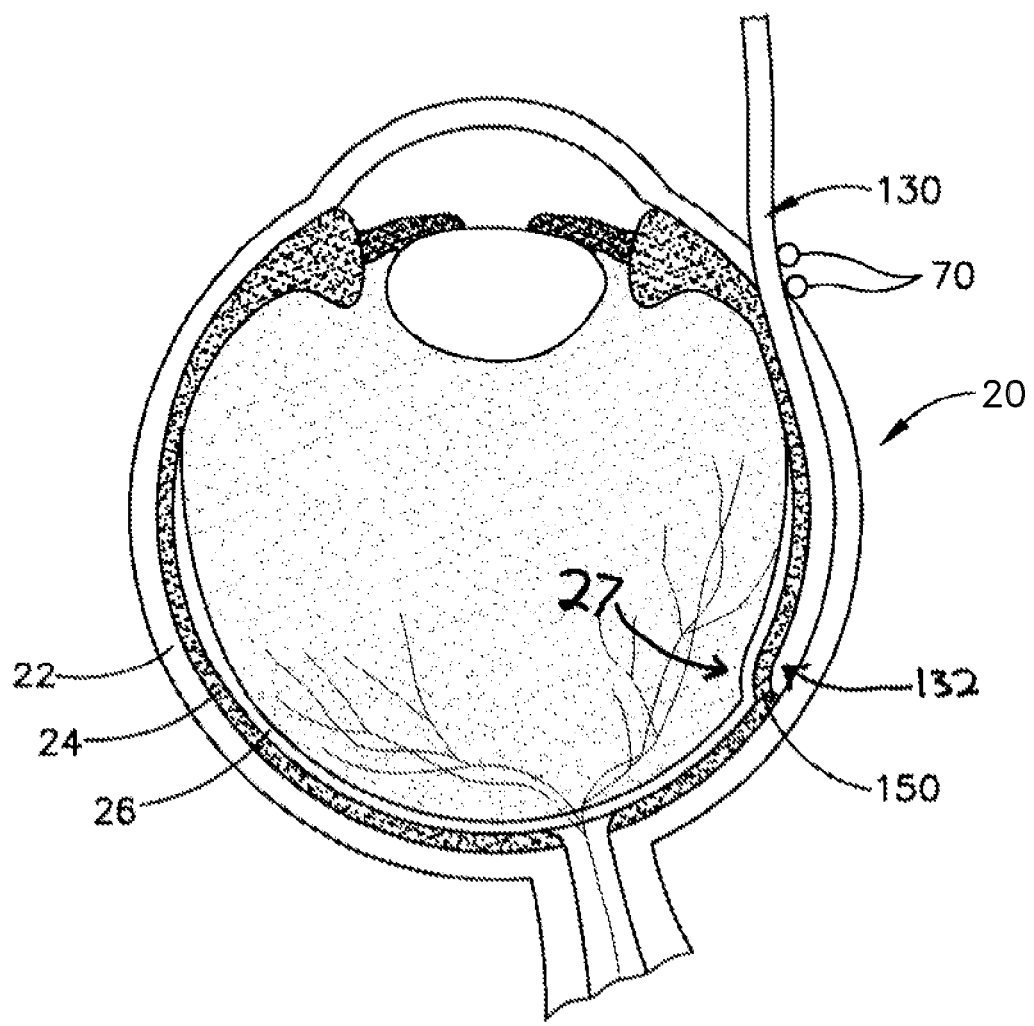
FIG. 4G depicts a cross-sectional side view of the eye of FIG. 4A, with the needle of FIG. 2B having aspirated a substantial portion of the dispensed leading bleb fluid of FIGS. 4E and 4F.

After providing the substantial separation of the retina (26) with bleb fluid (90), the operator may actuate fluid delivery system (80) to aspirate the bleb fluid (90) from the eye (20), as shown in FIG. 4G. In some versions, bleb fluid source (82) is capable of providing this aspiration, drawing the previously delivered bleb fluid (90) back toward bleb fluid source (82). In some other versions, fluid delivery system (80) includes a separate aspiration feature. Such a separate aspiration feature may include an active pump (e.g., a syringe, etc.) or a reservoir that is in fluid communication with atmosphere (e.g., relying on intraocular pressure to provide passive draining). In some versions, all the bleb fluid (90) is aspirated from the subretinal space. In some other versions, substantially all of the bleb fluid (90) is aspirated from the subretinal space, such that a very small portion (e.g., approximately 5 µL) of bleb fluid (90) is left in the subretinal space. Despite the aspiration of all or substantially all the bleb fluid (90) from the subretinal space, the detached portion (27) of the retina (26) remains detached from the choroid (26). This portion (27) may be visible to the operator as a "subretinal shadow."

In some versions, the aspiration step may be carried out after all the bleb fluid (90) has been delivered. Alternatively, aspiration may be provided between the actuations of fluid delivery system (80) to deliver the bleb fluid (90) in stages. For instance, a first volume of bleb fluid (90) may be delivered, followed by aspiration of some or all of that first volume of bleb fluid (90), followed by delivery of a second volume of bleb fluid (90). In some such versions, a second aspiration step may be carried out to aspirate some or all of that second volume of bleb fluid (90). In some other variations, the aspiration step(s) is/are omitted, such that no bleb fluid (90) is aspirated from the eye (20). It should therefore be understood that aspiration of bleb fluid (90) from the eye (20) is merely optional and may be omitted in some settings.

Figure 4H:
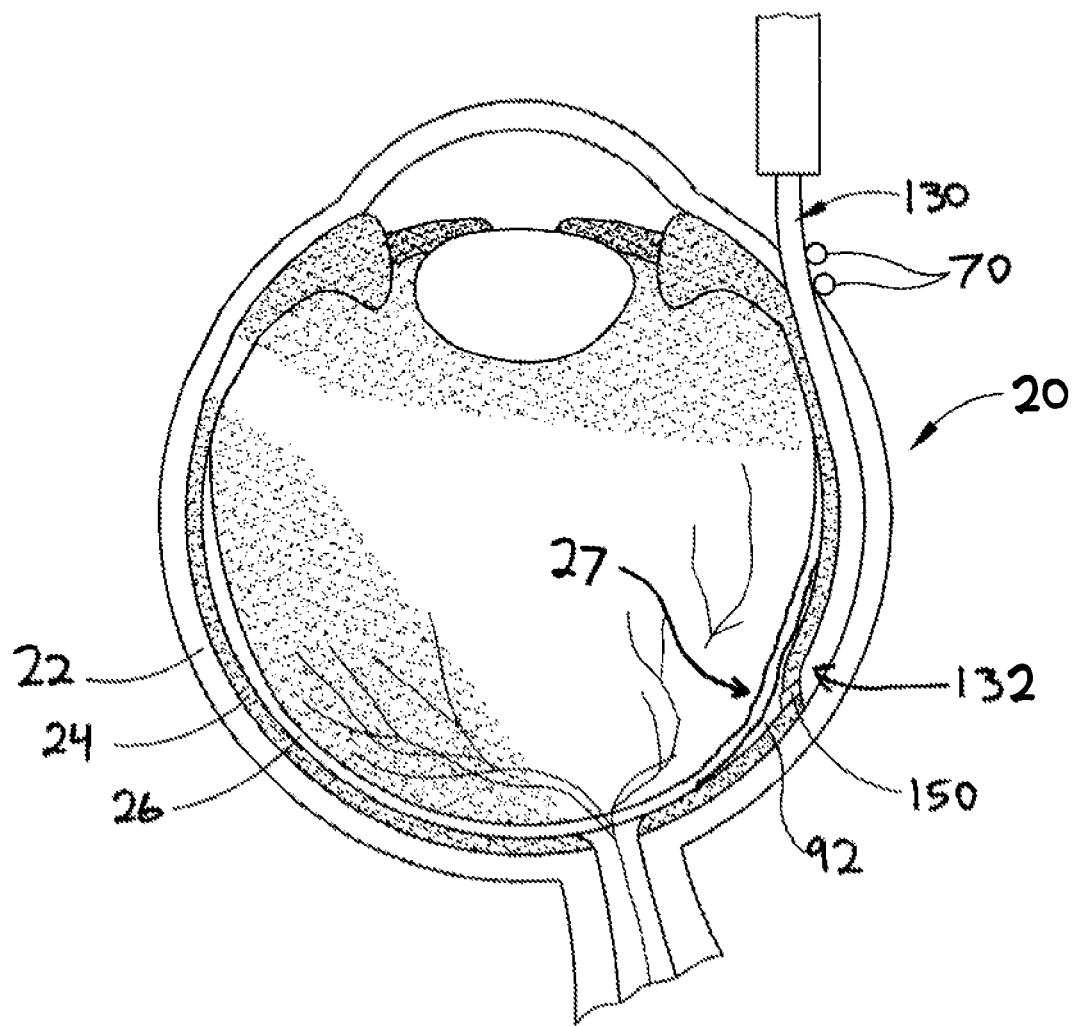
FIG. 4H depicts a cross-sectional side view of the eye of FIG. 4A, with the needle dispensing a therapeutic agent to the eye at the back of the eye, between the sclera and choroid.

After bleb fluid (90) has been aspirated from the subretinal space, or simply after the bleb fluid (90) has been delivered, the operator then actuates fluid delivery system (80) to drive the therapeutic agent (92) from therapeutic agent fluid source (84), thereby delivering the therapeutic agent (92) to the subretinal space as shown in FIG. 4H. By way of example only, approximately 25 µL of therapeutic agent (92) may be delivered to the subretinal space. By way of further example only, the volume of therapeutic agent (92) delivered to the subretinal space may be in the range of approximately 15 µL to approximately 300 µL, or more particularly in the range of approximately 10 µL to approximately 300 µL, or more particularly in the range of approximately 25 µL to approximately 200 µL, or more particularly in the range of approximately 15 µL to approximately 100 µL, or more particularly in the range of approximately 25 µL to approximately 100 µL. The delivered volume of therapeutic agent (92) disperses along the substantially large subretinal space (or "subretinal shadow") that is defined between the detached portion (27) of the retina (26) and the choroid (26).

The relatively large size of the detached portion (27) provides a correspondingly large surface area for distribution and absorption of the therapeutic agent (92) by the retina (26). In other words, the approximately 25 µL of therapeutic agent (92) covers the same surface area of detached portion (27) that was created by between approximately 50 µL and approximately 300 µL of bleb fluid (90). As another merely illustrative example, approximately 50 µL of therapeutic agent (92) may cover the surface area of detached portion (27) that was created by approximately 300 µL of bleb fluid (90). The relatively large surface area of the detached portion (27) provides a relatively large ratio of retina (26) surface area exposure to therapeutic agent (92) volume. This large surface area to volume ratio may in turn maximize the therapeutic benefits of the therapeutic agent (92) to the retina (26).

After a suitable volume of therapeutic agent (92) has been delivered to the subretinal space, the operator then actuates knob (120) to retract needle (150) proximally back into cannula (130); then pulls cannula (130) out of the eye (20). In the present example, because of the size of needle (150), the site where needle (150) penetrated through the choroid (24) is self-sealing, such that no further steps need be taken to seal the needle (150) puncture site through the choroid (24). Suture loop assembly (70) is removed from the eye (20), and the incision in the sclera (22) may be closed using any suitable conventional techniques.

Many therapeutic agents (92) whose mechanisms of action work within the cell layers surrounding the subretinal space, namely the retinal pigment epithelium (RPE) and photoreceptors, may require direct juxtaposition to these cells to maximize therapeutic response. By expanding the dissected volume of the subretinal space in accordance with the method described above, the delivered therapeutic agent (92) creates a thin layer of fluid rather than a spheroidal bleb; and increases the surface area of therapeutic agent (92) in contact with the RPE and photoreceptors. This increased distribution area may lead to enhanced therapeutic efficacy. One specific example is a retinal gene therapy application where a vector is used to transplant normal genes in place of missing or defective ones to address a retinal disorder or inherited retinal disease. In gene therapies applied to retinal disease, the transduction of the cells, subsequent expression of the gene, and restoration of normal function may occur in the area of subretinal delivery. The methods and instrument (100) described herein would enable subretinal delivery that maximizes the area of transduction for gene therapy applications while minimizing the effect of the focal retinal detachment caused by the subretinal delivery.

As noted above, the foregoing procedure may be carried out to treat a patient having macular degeneration. In some such instances, the therapeutic agent (92) that is delivered by needle (150) may comprise cells that are derived from postpartum umbilicus and placenta. As noted above, and by way of example only, the therapeutic agent (92) may be provided in accordance with at least some of the teachings of U.S. Pat. No. 7,413,734, the disclosure of which is incorporated by reference herein. Alternatively, needle (150) may be used to deliver any other suitable substance or substances, in addition to or in lieu of those described in U.S. Pat. No. 7,413,734 and/or elsewhere herein. The particular therapeutic agent (92) delivered in the above-described example may be any suitable therapeutic agent configured to treat an ocular condition. Some merely exemplary suitable therapeutic agents may include, but are not necessarily limited to, drugs having smaller or large molecules, therapeutic cell solutions, certain gene therapy solutions, tissue plasminogen activators, and/or any other suitable therapeutic agent as will be apparent to those of ordinary skill in the art in view of the teachings herein. It should also be understood that macular degeneration is just one merely illustrative example of a condition that may be treated through the procedure described herein. Other biological conditions that may be addressed using the instruments and procedures described herein will be apparent to those of ordinary skill in the art. It should be understood that instrument (100) and the exemplary methods described herein are not intended to necessarily be limited to treatment of the particular medical conditions that are specifically identified herein. A non-exhaustive, non-limiting listing of other conditions that may be addressed by instrument (100) and the exemplary methods described herein may include diabetic macular edema, inherited retinal diseases, retinitis pigmentosa, retinal vein occlusion, diabetic retinopathy, posterior uveitis, Stargardt disease, etc.

It should also be understood that the procedure described above may be carried out in accordance with any of the teachings of U.S. Pub. No. 2015/0223977, entitled "Method and Apparatus for Subretinal Administration of Therapeutic Agent," published Aug. 13, 2015, the disclosure of which is incorporated by reference herein; U.S. Pub. No. 2015/0351958, entitled "Therapeutic Agent Delivery Device with Convergent Lumen," published Dec. 10, 2015, the disclosure of which is incorporated by reference herein; U.S. Pub. No. 2015/0351959, entitled "Sub-Retinal Tangential Needle Catheter Guide and Introducer," published Dec. 10, 2015, the disclosure of which is incorporated by reference herein; U.S. Pub. No. 2016/0074212, entitled "Method and Apparatus for Sensing Position Between Layers of an Eye," published Mar. 17, 2016, the disclosure of which is incorporated by reference herein; U.S. Pub. No. 2016/0074217, entitled "Motorized Suprachoroidal Injection of Therapeutic Agent," published Mar. 17, 2016, the disclosure of which is incorporated by reference herein; U.S. Pub. No. 2016/0074211, entitled "Therapeutic Agent Delivery Device with Advanceable Cannula and Needle," published Mar. 17, 2016, the disclosure of which is incorporated by reference herein; U.S. Pub. No. 2016/0081849, entitled "Therapeutic Agent Delivery Device," published Mar. 24, 2016, the disclosure of which is incorporated by reference herein; and/or U.S. Pub. No. 2018/0256394, entitled "Method of Performing Subretinal Drainage and Agent Delivery," published Sep. 13, 2018, the disclosure of which is incorporated by reference herein.

B. Exemplary Subretinal Delivery of Substantial Volume of Leading Bleb Fluid from Plurality of Suprachoroidal Sites As noted above, a variation of the procedure shown in FIGS. 4A-4H may include the delivery of leading bleb fluid (90) from a plurality of site instead of delivering bleb fluid (90) from only one single site. FIGS. 5A-6B depict an exemplary procedure in which leading bleb fluid (90) is delivered to the subretinal space from more than one site in the suprachoroidal space. Delivering bleb fluid (90) from more than one site instead of just one single site may be preferable for various reasons. For instance, in some cases, delivering a substantial amount of bleb fluid (90) from just one single site may cause the detached portion (27) of the retina (26) to stretch, which may be undesirable. Delivering the same total volume of bleb fluid (90) from two or more sites may reduce the risk of stretching in the detached portion (27) of the retina (26).

Moreover, delivering a certain total volume of bleb fluid (90) from two or more sites may ultimately result in a detached portion (27) of the retina (26) with a surface area that is larger than the surface area that could be achieved by delivering the same volume of bleb fluid (90) from just one single site. To show this, one may assume that a delivered volume of bleb fluid (90) will be captured under a detached portion (27) substantially in the form of a hemisphere. With this assumption, one may determine the radius of the detached portion (27) based on the volume of bleb fluid (90) using the following equation showing the calculation of the volume of a hemisphere:

$$V=(2/3)\pi r^3$$

Since the volume of the hemisphere formed by detached portion (27) will be the same as the volume of delivered bleb fluid (90), the radius of a hemisphere of 100 μL of delivered bleb fluid (90) will be approximately 3.6 mm. With that radius known, one may determine the surface area of the hemisphere, including the convex surface of the hemisphere and the flat surface of the hemisphere, using the following equation:

$$A=3\pi r^2$$

Continuing with the example of a 100 μL volume of delivered bleb fluid (90), the surface area of the hemisphere will be approximately 41.4 mm². In other words, the delivered bleb fluid (90) will contact approximately 41.4 mm² of ocular tissue, including the retina (26) and the choroid (24). After the therapeutic agent (92) is delivered, the delivered therapeutic agent (92) may also contact the same approximately 41.4 mm² of ocular tissue. In other words, the 100 μL volume of delivered bleb fluid (90) will create a detached portion (27) of the retina (26) that provides an area of approximately 41.4 mm² of ocular tissue for the delivered therapeutic agent (92) to contact.

In view of the foregoing, one may compare the total surface area of ocular tissue under a detached portion (27) of the retina (26) as provided by a single delivered 200 volume of bleb fluid (90) versus the total surface area of ocular tissue under a detached portion (27) of the retina (26) as provided by two separately delivered 100 μL volumes of bleb fluid (90). Applying the equations provided above, the single delivered 200 μL volume of bleb fluid (90) will provide a total surface area of approximately 65.6 mm². By contrast, the two delivered 100 μL volumes of bleb fluid (90) will provide a total surface area of approximately 82.7 mm². Thus, even though the total volume of delivered bleb fluid (90) in both scenarios is 200 the breakup into two separate deliveries results in a substantially larger surface area of ocular tissue that can be subsequently contacted by the delivered therapeutic agent (92).

As noted below, the separate delivery sites for bleb fluid (90) may be far enough apart such that the corresponding resulting hemispheres under the detached portion (27) of the retina (26) remain isolated from each other, such that the retina (26) is detached from the choroid (24) in a plurality of discrete regions. Alternatively, separate delivery sites for bleb fluid (90) may be close enough such that the corresponding resulting hemispheres under the detached portion (27) of the retina (26) merge with each other, resulting in a single continuous region of the detached portion (27). In such scenarios, the total surface area of ocular tissue that can be subsequently contacted by the delivered therapeutic agent (92) may not necessarily be exactly equal to the sum of each $A=3\pi r^2$ calculation associated with each separately delivered volume of bleb fluid (90). However, even in these scenarios, the total surface area of ocular tissue that can be subsequently contacted by the delivered therapeutic agent (92) may still exceed the total surface area of ocular tissue that could be subsequently contacted by the delivered therapeutic agent (92) after having the same total volume of bleb fluid (90) being delivered to just one single site.

Figure 5A:
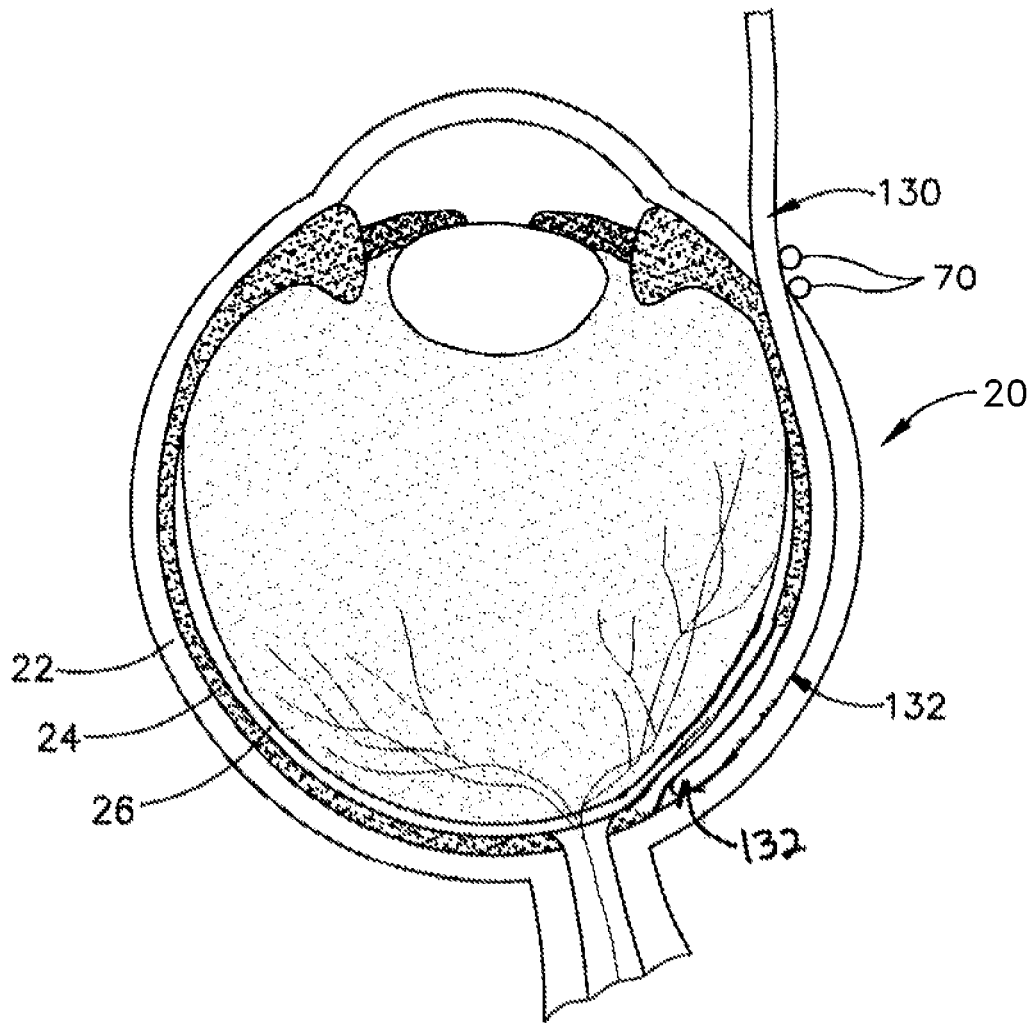
FIG. 5A depicts a cross-sectional side view of the eye of FIG. 4A, with the cannula of FIG. 2A being inserted through a sclerotomy opening and in between the sclera and choroid of the eye, with the distal end of the cannula at a first position.
Figure 5B:
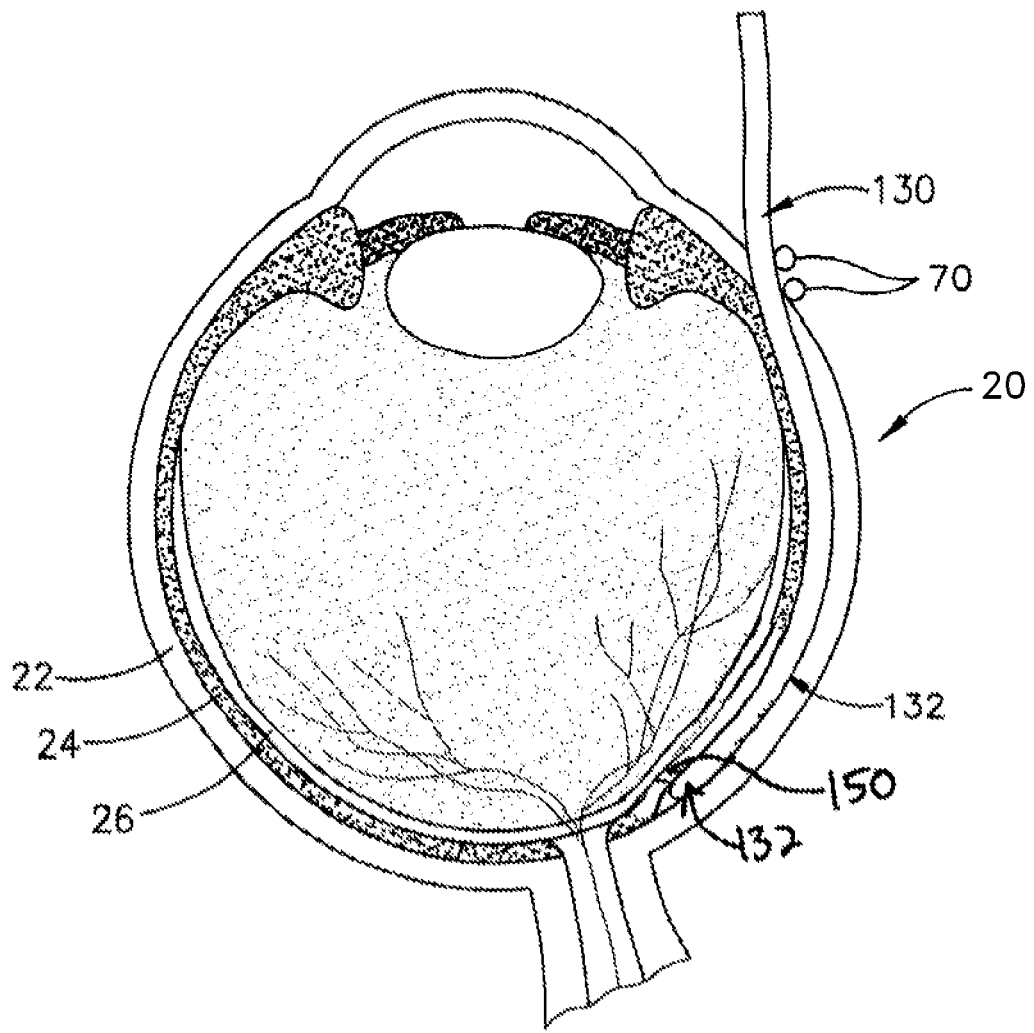
FIG. 5B depicts a cross-sectional side view of the eye of FIG. 4A, with the distal end of the cannula at the first position, and with the needle of FIG. 2B being advanced through the choroid to access the subretinal space from the first position.
Figure 5C:
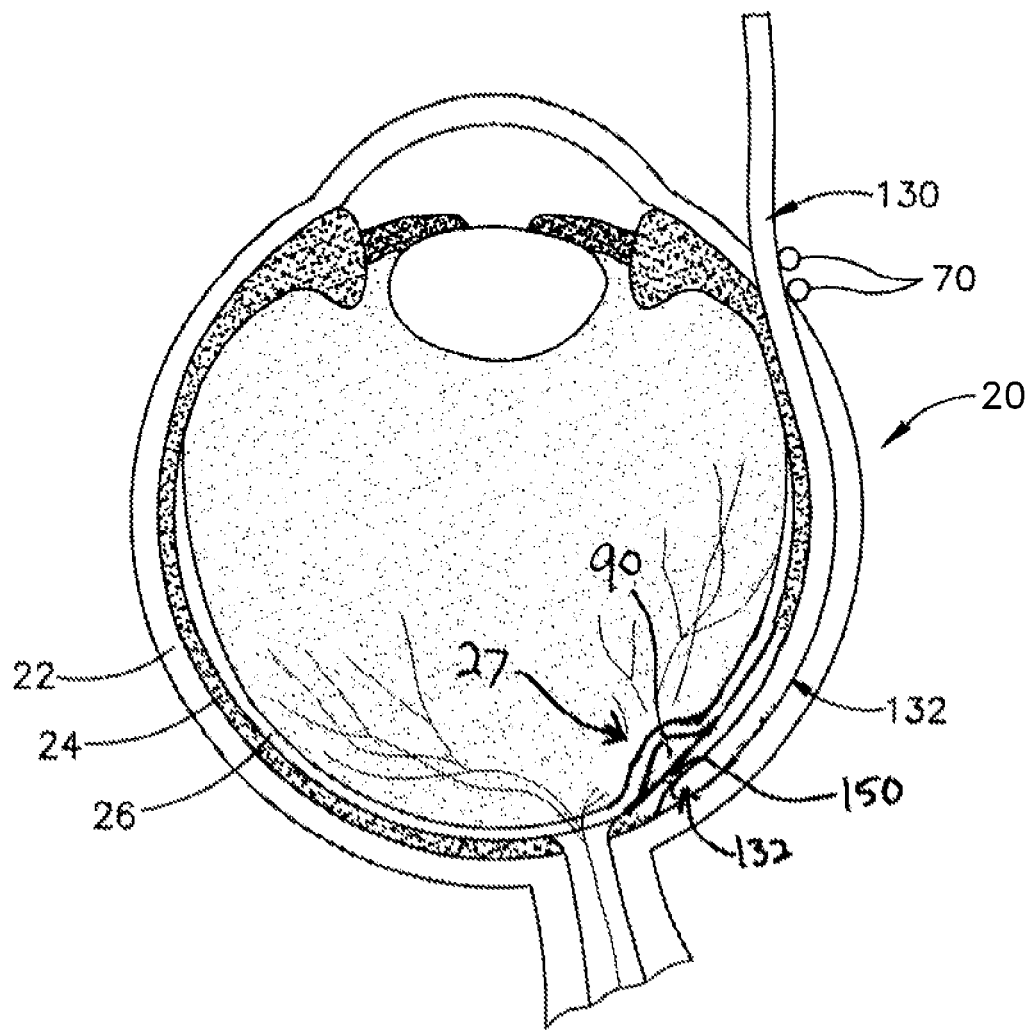
FIG. 5C depicts a cross-sectional side view of the eye of FIG. 4A, with the needle of FIG. 2B dispensing a first volume of leading bleb fluid from the first position to provide separation between a first region of the retina and the choroid.

FIGS. 5A-5F show an exemplary procedure in which two volumes of bleb fluid (90) are delivered from two different sites. The stage shown in FIG. 5A may take place right after the stage shown in 4B and described above. As shown in FIG. 5A, cannula (130) is directed through suture loop assembly (70) and into the sclerotomy incision. Cannula (130) is advanced until distal end (132) is located at a first position at the posterior region of the retina (26). Various suitable ways of visualizing distal end (132) to thereby observe proper positioning of distal end (132) will be apparent to those of ordinary skill in the art in view of the teachings herein. Once cannula (130) has been advanced to the position shown in FIG. 5A, the operator may advance needle (150) of instrument (100) distally as described above by actuating knob (120). As can be seen in FIG. 5B, needle (150) is advanced relative to cannula (130) such that needle (150) pierces through the choroid (24) without penetrating the retina (26). The operator then actuates fluid delivery system (80) to drive bleb fluid from bleb fluid source (82), thereby delivering a first volume of bleb fluid (90) to the subretinal space from the first position, as shown in FIG. 5C. This forms a first region of a detached portion (27) of the retina (26).

Figure 5D:
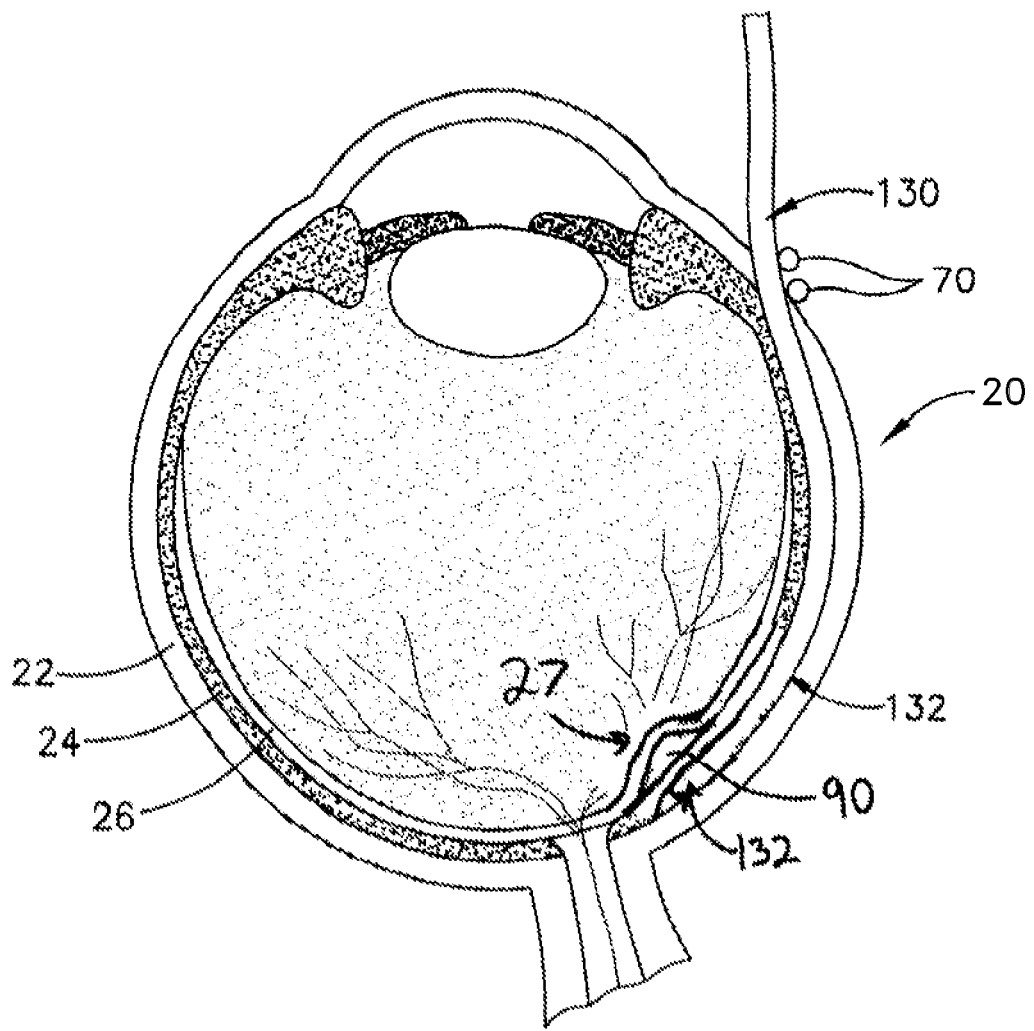
FIG. 5D depicts a cross-sectional side view of the eye of FIG. 4A, with the distal end of the cannula at the first position, and with the needle of FIG. 2B being retracted back into the cannula after dispensing the first volume of leading bleb fluid.
Figure 5E:
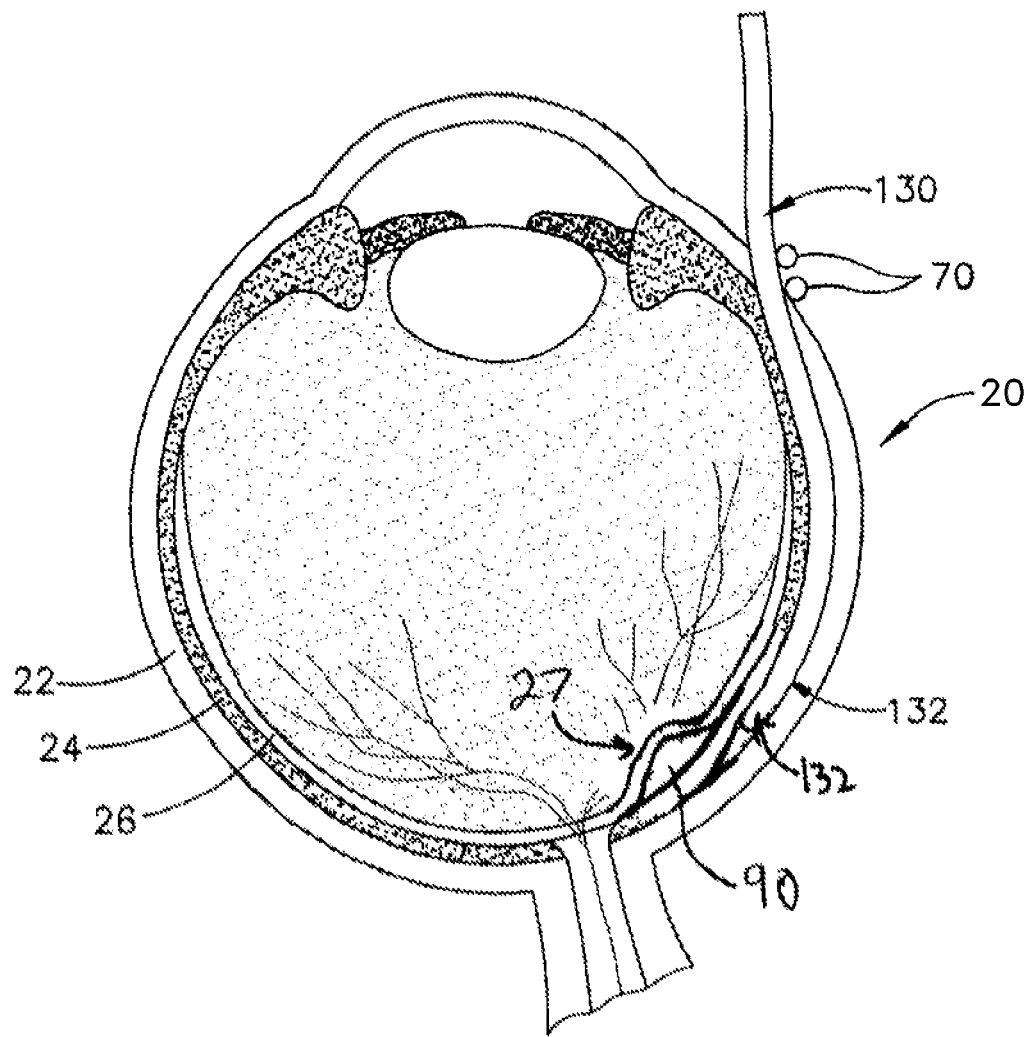
FIG. 5E depicts a cross-sectional side view of the eye of FIG. 4A, with the distal end of the cannula at a second position between the sclera and choroid of the eye.
Figure 5F:
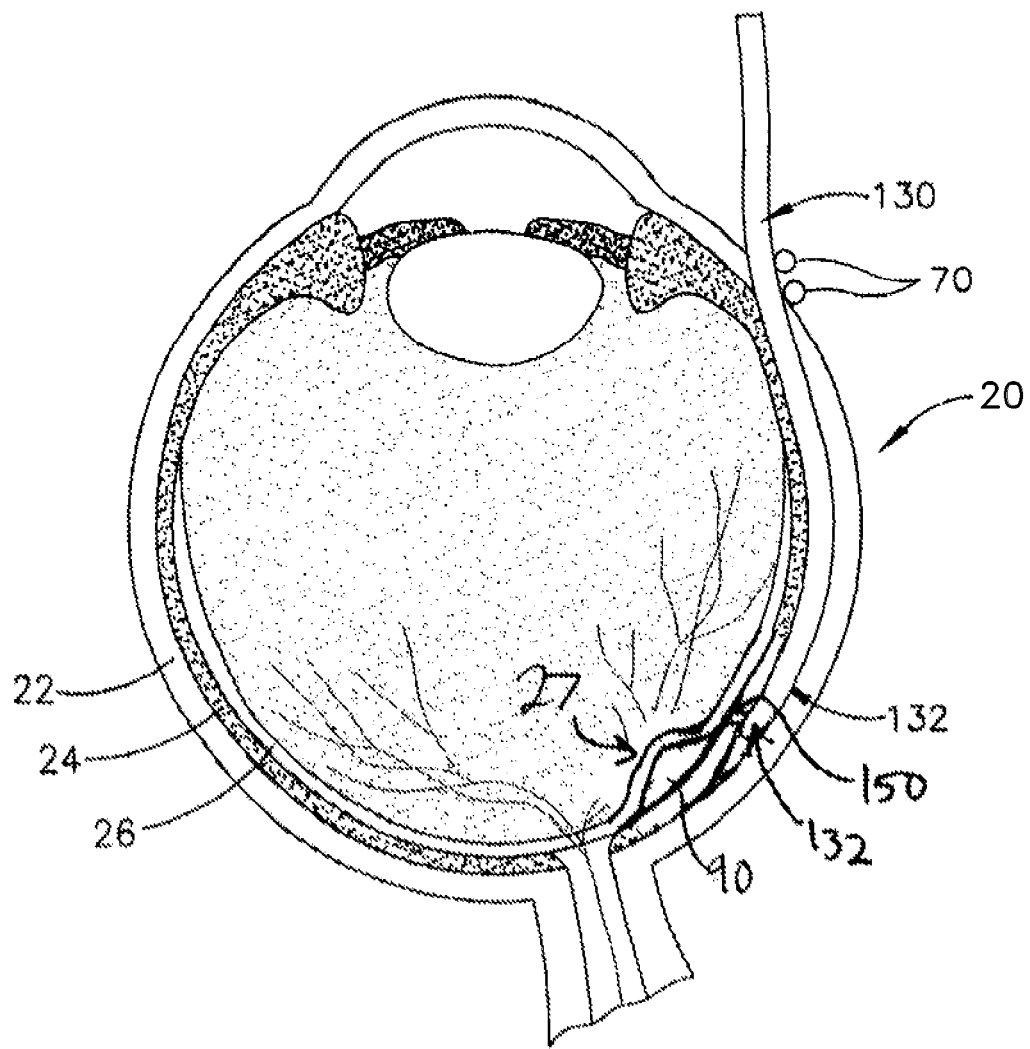
FIG. 5F depicts a cross-sectional side view of the eye of FIG. 4A, with the distal end of the cannula at the second position, and with the needle of FIG. 2B being advanced through the choroid to access the subretinal space from the second position.
Figure 5G:
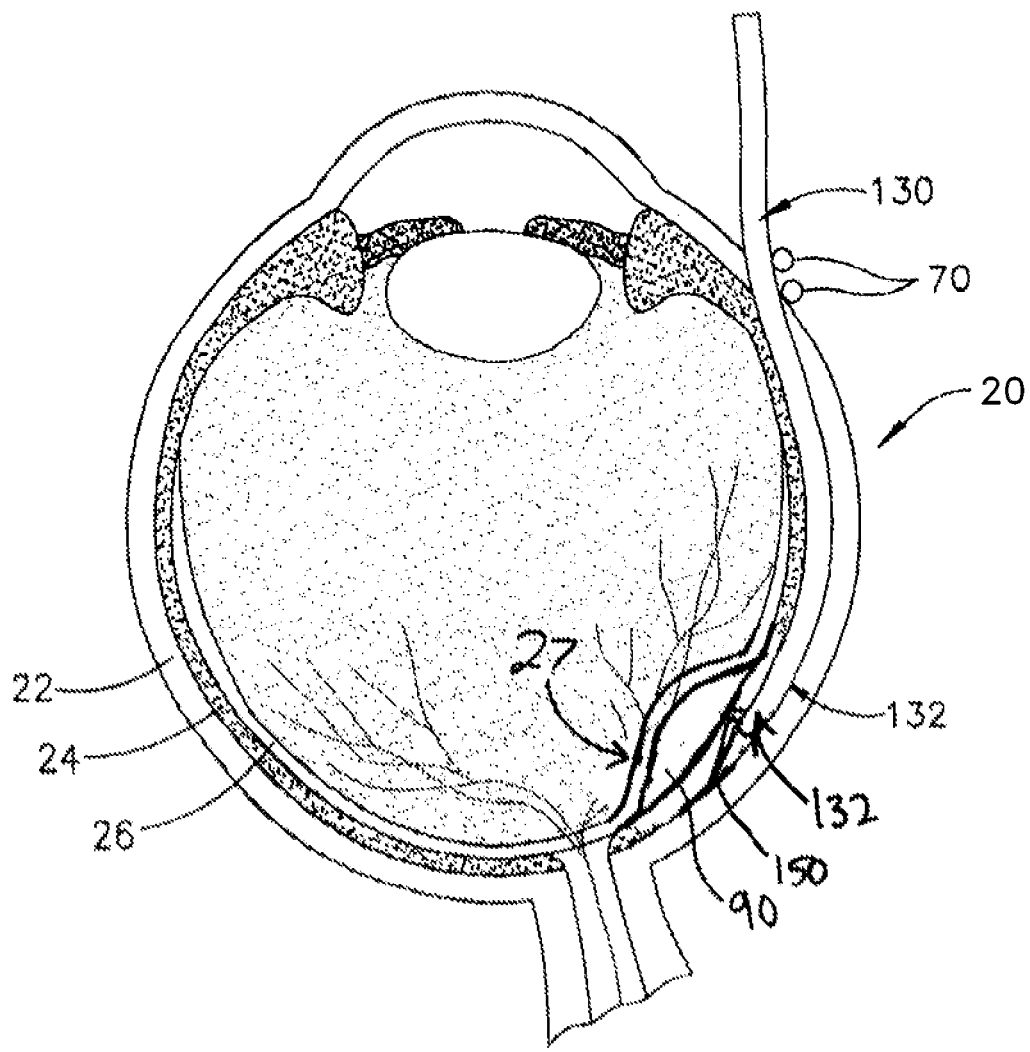
FIG. 5G depicts a cross-sectional side view of the eye of FIG. 4A, with the needle of FIG. 2B dispensing a first volume of leading bleb fluid from the first position to provide separation between a first region of the retina and the choroid.

After delivering the first volume of bleb fluid (90), the operator may actuate knob (120) to retract needle (150) back into cannula (132), as shown in FIG. 5D. The operator may then pull cannula (132) to locate distal end (132) at a second position at the posterior region of the retina (26), as shown in FIG. 5E. Once cannula (130) has been located at the position shown in FIG. 5E, the operator may again advance needle (150) of instrument (100) distally as described above by actuating knob (120). As can be seen in FIG. 5F, needle (150) is advanced relative to cannula (130) such that needle (150) pierces through the choroid (24) without penetrating the retina (26). The operator then actuates fluid delivery system (80) to drive bleb fluid from bleb fluid source (82), thereby delivering a second volume of bleb fluid (90) to the subretinal space from the second position, as shown in FIG. 5G. This forms a second region of a detached portion (27) of the retina (26). In this example, the first and second delivery positions are substantially close to each other such that the two volumes of delivered bleb fluid (90) effectively merge with each other to form a collectively detached portion (27) of the retina (26). In some other versions, the first and second delivery positions are far enough from each other such that the two volumes of delivered bleb fluid (90) remain isolated from each other to form corresponding discrete detached portions (27) of the retina (26).

After reaching the stage shown in FIG. 5G, the delivered bleb fluid (90) may be aspirated away as shown and described above with reference to FIG. 4G. This is merely optional and is not necessarily required. Either way, needle (150) may be used to deliver the therapeutic agent (92) to the region under detached portion (27) as described above with reference to FIG. 4H. The total surface area of ocular tissue that can be contacted by the delivered therapeutic agent (92) may exceed the total surface area of ocular tissue that could otherwise be subsequently contacted by the delivered therapeutic agent (92) after having the same total volume of bleb fluid (90) being delivered from just one single delivery position. In other words, if the same total volume of bleb fluid (90) is delivered in the procedure shown in FIGS. 5A-5G as the total volume of bleb fluid (90) delivered in the procedure shown in FIGS. 4A-4F, the procedure shown in FIGS. 5A-5G may provide a greater surface area of ocular tissue for contact with the therapeutic agent (92) than the corresponding surface area of ocular tissue provided by the procedure shown in FIGS. 4A-4F. Moreover, the procedure shown in FIGS. 5A-5G may impart less tensile stress on the retina (26) than the tensile stress imparted on the retina (26) by the procedure shown in FIGS. 4A-4F, such that the procedure shown in FIGS. 5A-5G may reduce the risk of stretching the retina (26).

Figure 6A:
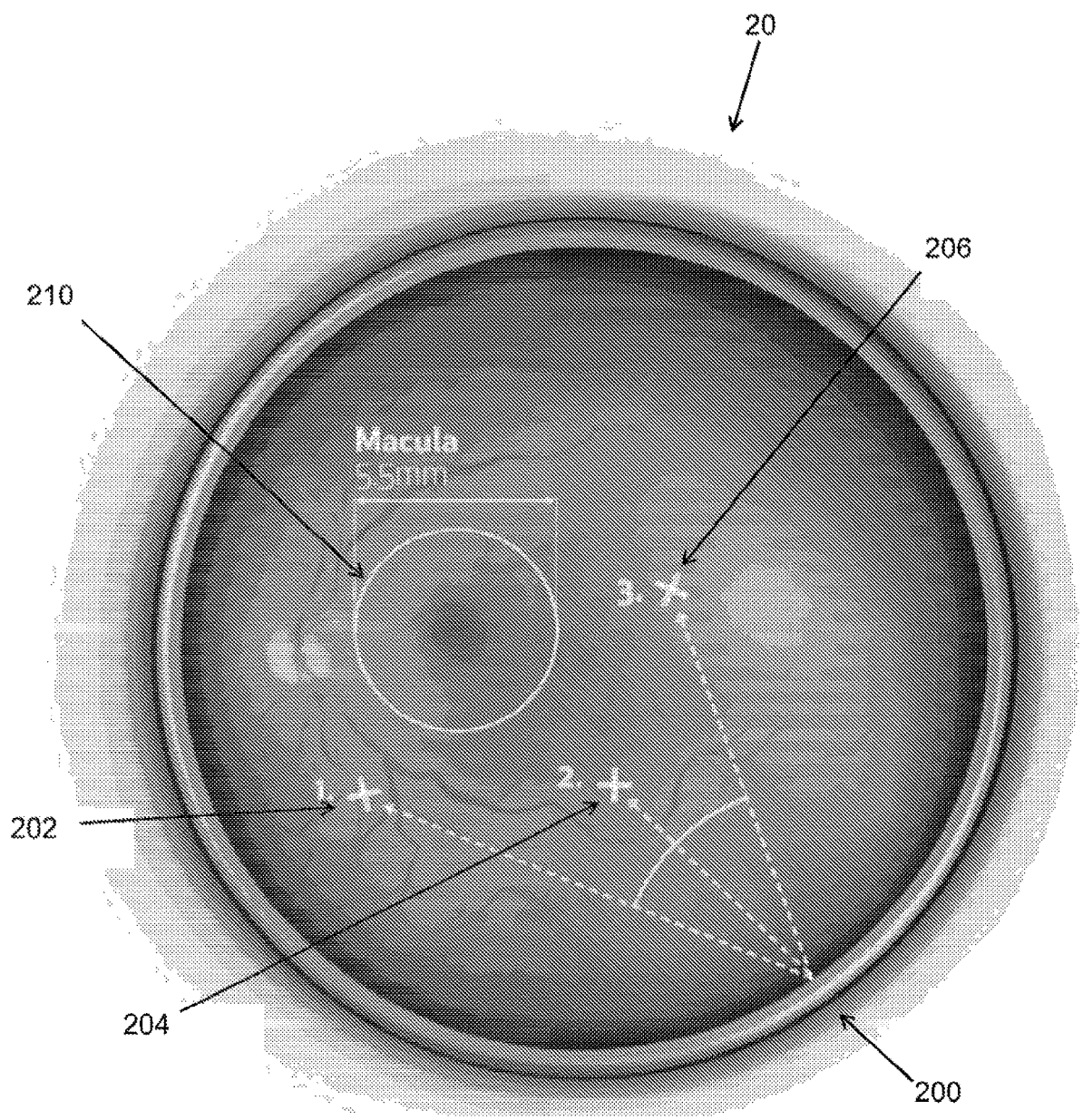
FIG. 6A depicts a cross-sectional top view of the eye of FIG. 4A, schematically depicting an exemplary set of leading bleb delivery sites between corresponding regions of the retina and the choroid.
Figure 6B:
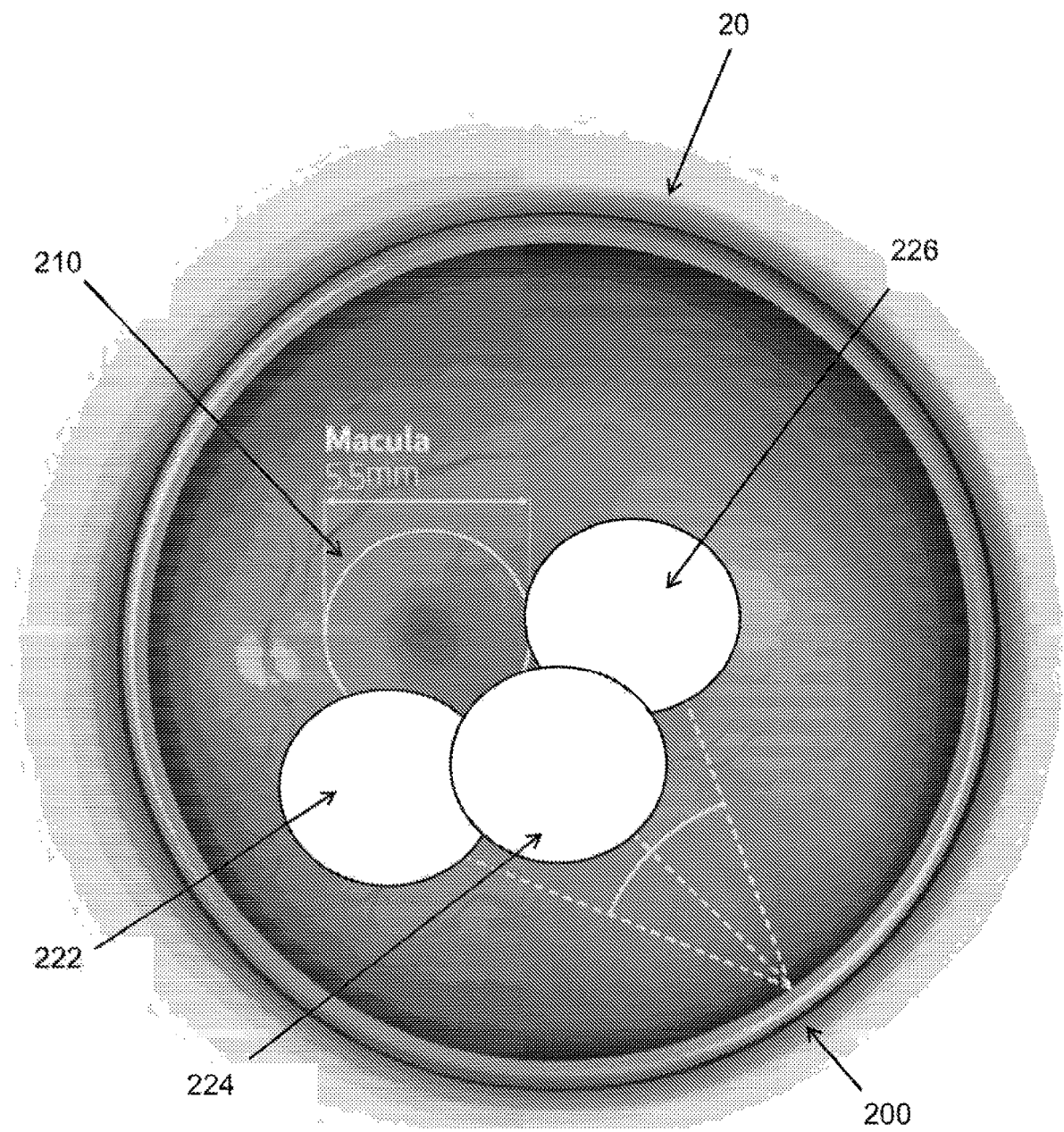
FIG. 6B depicts a cross-sectional top view of the eye of FIG. 4A, schematically depicting leading bleb fluid delivered at the delivery sites of FIG. 6A.

While the above-described procedure of FIGS. 5A-5G provides leading bleb (90) delivery sites that are spaced apart from each other in an anterior-posterior relationship, it should be understood that the leading bleb (90) delivery sites may be spaced apart form each other in any other suitable fashion. By way of example only, FIG. 6A shows three delivery sites (202, 204, 206) that may be accessed from a single sclerotomy insertion point (200). In this example, the three delivery sites (202, 204, 206) are generally positioned around the macula (210) of the eye (20). These delivery sites (202, 204, 206) are not necessarily anterior or posterior to each other. In order to reach these delivery sites (202, 204, 206), cannula (130) may first be inserted to position distal end (132) at the first delivery site (202); then be slightly retracted and pivoted at the sclerotomy to position distal end (132) at the second delivery site (204); then be pivoted at the sclerotomy again and then be advanced to position distal end (132) at the third delivery site (206). As shown in FIG. 6B, when bleb fluid (90) is delivered to each of these delivery sites (202, 204, 206), the resulting bleb regions (222, 224, 226) are adjacent to each other around the macula (210). As noted above, these bleb regions (222, 224, 226) may merge with each other to create one continuous detached portion (27) of the retina (26). Alternatively, these bleb regions (222, 224, 226) may remain isolated from each other to three corresponding discrete detached portions (27) of the retina (26).

In versions of the procedures shown in FIGS. 5A-6B where the separately delivered volumes of bleb fluid (90) result in discrete detached portions (27) of the retina (26), the therapeutic agent (92) may be delivered under each discrete detached portion (27) of the retina (26). In some instances, the therapeutic agent (92) may be delivered immediately after each volume of bleb fluid (90) is delivered, such that a first volume of therapeutic agent (92) is delivered to a first site immediately after the first volume of bleb fluid (90) is delivered to the first site, before the second volume of bleb fluid (90) is delivered to the second site. Alternatively, all separate volumes of bleb fluid (90) may be delivered first; and then therapeutic agent (92) may be delivered. This procedure may be used to determine the extent to which the delivered volumes of bleb fluid (90) merge with each other, such that only a single volume of therapeutic agent (92) needs to be delivered to any region associated with merged volumes of bleb fluid (90).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method, comprising: (a) inserting a flexible cannula between a sclera and a choroid of an eye; (b) advancing a needle from a distal end of the flexible cannula, such that the needle pierces the choroid to access a subretinal space of the eye; (c) delivering a first volume of a leading bleb fluid to the subretinal space via the needle; (d) ceasing delivery of the leading bleb fluid to the subretinal space for a duration of time; and (e) after expiration of the duration of time, delivering a second volume of the leading bleb fluid to the subretinal space via the needle; wherein the combination of the delivered first and second volumes of the leading bleb fluid causes a substantial portion of the retina to detach from the choroid.

Example 2

The method of Example 1, further comprising delivering a therapeutic agent to the subretinal space after delivering the second volume of the leading bleb fluid.

Example 3

The method of Example 2, wherein the therapeutic agent is delivered via the needle.

Example 4

The method of any one or more of Examples 2 through 3, wherein the act of delivering the therapeutic agent comprises delivering a third volume of the therapeutic agent, wherein the combination of the first volume and the second volume is larger than the third volume.

Example 5

The method of any one or more of Examples 1 through 4, further comprising aspirating at least some of the delivered leading bleb fluid from the subretinal space after delivering the first volume of the leading bleb fluid.

Example 6

The method of any one or more of Examples 1 through 5, further comprising aspirating at least some of the delivered leading bleb fluid from the subretinal space after delivering the second volume of the leading bleb fluid.

Example 7

The method of any one or more of Examples 1 through 6, wherein the first volume of the leading bleb fluid is equal to the second volume of the leading bleb fluid.

Example 8

The method of any one or more of Examples 1 through 7, wherein the first volume of leading bleb fluid is different from the second volume of the leading bleb fluid.

Example 9

The method of any one or more of Examples 1 through 8, wherein the needle remains stationary during the acts of delivering the first volume of leading bleb fluid, ceasing delivery, and delivering the second volume of the leading bleb fluid.

Example 10

The method of any one or more of Examples 1 through 9, further comprising repositioning the flexible cannula and the needle between the acts of delivering the first volume of the leading bleb fluid and delivering the second volume of the leading bleb fluid, such that the flexible cannula and the needle are repositioned while ceasing delivery of the leading bleb fluid to the subretinal space.

Example 11

The method of Example 10, wherein the delivered first and second volumes are positioned in sufficient proximity to merge with each other in the subretinal space.

Example 12

The method of any one or more of Examples 1 through 11, wherein the first volume is from approximately 25 µL to approximately 350 µL.

Example 13

The method of Example 12, wherein the second volume is from approximately 25 to approximately 350 µL.

Example 14

The method of any one or more of Examples 1 through 13, wherein the first volume is from approximately 75 µL to approximately 150 µL.

Example 15

The method of Example 14, wherein the second volume is from approximately 75 to approximately 150 µL.

Example 16

The method of any one or more of Examples 1 through 15, further comprises performing a sclerotomy in the sclera to thereby form an incision the sclera, wherein the act of inserting the flexible cannula between the sclera and the choroid comprises inserting the cannula through the incision.

Example 17

The method of any one or more of Examples 1 through 16, further comprising securing a guide assembly to the eye, wherein the act of inserting the flexible cannula between the sclera and the choroid comprises inserting the cannula through the guide assembly.

Example 18

The method of any one or more of Examples 1 through 17, wherein the distal end of the flexible cannula includes a transversely oriented opening, wherein the act of advancing the needle comprises advancing the needle out through the transversely oriented opening.

Example 19

The method of any one or more of Examples 1 through 18, wherein the needle does not pierce a retina of the eye when the needle is advanced from the distal end of the flexible cannula.

Example 20

A method, comprising: (a) inserting a flexible cannula between a sclera and a choroid of an eye; (b) advancing a needle from a distal end of the flexible cannula, such that the needle pierces the choroid to access a subretinal space of the eye; (c) injecting a first volume of bleb fluid into the subretinal space via the needle; (d) injecting a second volume of bleb fluid into the subretinal space via the needle; and (e) injecting a third volume of therapeutic agent into the subretinal space via the needle.

IV. Miscellaneous

It should be understood that any of the versions of the instruments described herein may include various other features in addition to or in lieu of those described above. By way of example only, any of the devices herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention claimed is:

1. A method, comprising:
   (a) inserting a flexible cannula between a sclera and a choroid of an eye;
   (b) advancing a needle from a distal end of the flexible cannula, such that the needle pierces the choroid to access a subretinal space of the eye;
   (c) delivering a first volume of a leading bleb fluid to the subretinal space via the needle;
   (d) ceasing delivery of the leading bleb fluid to the subretinal space for a duration of time;
   (e) after expiration of the duration of time, delivering a second volume of the leading bleb fluid to the subretinal space via the needle, and
   (f) repositioning the flexible cannula and the needle between the delivering the first volume of the leading bleb fluid and the delivering the second volume of the leading bleb fluid, such that the flexible cannula and the needle are repositioned while ceasing delivery of the leading bleb fluid to the subretinal space and while the flexible cannula remains between the sclera and the choroid of the eye,
   wherein the delivered first volume of the leading bleb fluid causes a portion of a retina of the eye to detach from the choroid, the detached portion of the retina having a surface area,
   wherein the delivered second volume of the leading bleb fluid causes the surface area of the detached portion of the retina to substantially increase.

2. The method of claim 1, further comprising delivering a therapeutic agent to the subretinal space after delivering the second volume of the leading bleb fluid.

3. The method of claim 2, wherein the therapeutic agent is delivered via the needle.

4. The method of claim 2, wherein the delivering the therapeutic agent comprises delivering a third volume of fluid, the third volume of fluid including the therapeutic agent, wherein the combination of the first volume and the second volume is larger than the third volume.

5. The method of claim 1, further comprising aspirating at least some of the delivered leading bleb fluid from the subretinal space after delivering the first volume of the leading bleb fluid.

6. The method of claim 1, further comprising aspirating at least some of the delivered leading bleb fluid from the subretinal space after delivering the second volume of the leading bleb fluid.

7. The method of claim 1, wherein the first volume of the leading bleb fluid is equal to the second volume of the leading bleb fluid.

8. The method of claim 1, wherein the first volume of leading bleb fluid is different from the second volume of the leading bleb fluid.

9. The method of claim 1, wherein the delivered first and second volumes are positioned in sufficient proximity to merge with each other in the subretinal space.

10. The method of claim 1, wherein the first volume is from 25 µL to 350 µL.

11. The method of claim 10, wherein the second volume is from 25 µL to 350 µL.

12. The method of claim 1, wherein the first volume is from 75 µL to 150 µL.

13. The method of claim 12, wherein the second volume is from 75 µL to 150 µL.

14. The method of claim 1, further comprising performing a sclerotomy in the sclera to thereby form an incision the sclera, wherein the inserting the flexible cannula between the sclera and the choroid comprises inserting the cannula through the incision.

15. The method of claim 1, further comprising securing a guide assembly to the eye, wherein the inserting the flexible cannula between the sclera and the choroid comprises inserting the cannula through the guide assembly.

16. The method of claim 1, wherein the distal end of the flexible cannula includes a transversely oriented opening, wherein the advancing the needle comprises advancing the needle out through the transversely oriented opening.

17. The method of claim 1, wherein the delivered second volume of the leading bleb fluid causes the surface area of the detached portion of the retina to substantially increase to be within a range of approximately 12 mm$^2$ to approximately 450 mm$^2$.

18. A method, comprising:
(a) inserting a flexible cannula to a first position between a sclera and a choroid of an eye;
(b) advancing a needle from a distal end of the flexible cannula, such that the needle pierces the choroid to access a first region of a subretinal space of the eye;
(c) injecting a first volume of bleb fluid into the subretinal space via the needle;
(d) repositioning the flexible cannula to a second position between the sclera and the choroid of the eye, wherein the repositioning comprises retracting the flexible cannula toward an insertion point of the flexible cannula into the eye while the flexible cannula remains between the sclera and the choroid of the eye, and then pivoting the flexible cannula at the insertion point of the flexible cannula into the eye while the flexible cannula remains between the sclera and the choroid of the eye;
(e) injecting a second volume of bleb fluid into a second region of the subretinal space via the needle; and
(f) injecting a third volume of therapeutic agent into the subretinal space via the needle.

19. A method, comprising:
(a) inserting a flexible cannula between a sclera and a choroid of an eye;
(b) advancing a needle from a distal end of the flexible cannula, such that the needle pierces the choroid to access a subretinal space of the eye;
(c) delivering a first volume of a leading bleb fluid to the subretinal space via the needle;
(d) ceasing delivery of the leading bleb fluid to the subretinal space;
(e) aspirating at least some of the delivered leading bleb fluid from the subretinal space after delivering the first volume of the leading bleb fluid; and
(f) after aspirating at least some of the delivered leading bleb fluid from the subretinal space, delivering a second volume of the leading bleb fluid to the subretinal space via the needle,
wherein the combination of the delivered first and second volumes of the leading bleb fluid causes a substantial portion of a retina to detach from the choroid.

* * * * *